(12) United States Patent
Miron et al.

(10) Patent No.: US 8,318,441 B2
(45) Date of Patent: Nov. 27, 2012

(54) FIBRINOGEN ALPHA AND HEMOGLOBIN POLYPEPTIDES AS CANCER MARKERS

(75) Inventors: Alexander Miron, Chestnut Hill, MA (US); James Dirk Iglehart, Newton, MA (US); Lyndsay N. Harris, Madison, CT (US); Xin Lu, Cambridge, MA (US); Qian Shi, Brighton, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 77 days.

(21) Appl. No.: 12/753,527

(22) Filed: Apr. 2, 2010

(65) Prior Publication Data
US 2010/0248271 A1    Sep. 30, 2010

Related U.S. Application Data

(63) Continuation of application No. 11/920,494, filed as application No. PCT/US2006/019124 on May 16, 2006, now abandoned.

(60) Provisional application No. 60/681,508, filed on May 16, 2005.

(51) Int. Cl.
*G01N 33/53* (2006.01)
(52) U.S. Cl. ......................................... 435/7.1
(58) Field of Classification Search .................. None
See application file for complete search history.

(56) References Cited

U.S. PATENT DOCUMENTS

| | | | |
|---|---|---|---|
| 4,230,767 A | 10/1980 | Isaka et al. | |
| 4,233,402 A | 11/1980 | Maggio et al. | |
| 4,275,149 A | 6/1981 | Litman et al. | |
| 4,376,110 A | 3/1983 | David et al. | |
| 4,659,678 A | 4/1987 | Forrest et al. | |
| 4,727,022 A | 2/1988 | Skold et al. | |
| 2007/0224201 A1 | 9/2007 | Wu et al. | |

FOREIGN PATENT DOCUMENTS

| | | |
|---|---|---|
| WO | WO-0113117 A2 | 2/2001 |
| WO | WO 02/090991 A2 * | 11/2002 |
| WO | WO-02090991 A2 | 11/2002 |
| WO | WO-2004053077 A2 | 6/2004 |
| WO | WO-2004090550 A2 | 10/2004 |

OTHER PUBLICATIONS

Tockman et al (Cancer Res., 1992, 52:2711s-2718s).*
Villanueva et al (JCI, 2006, 116(1): 271-284).*
Ambroise et al., "Selection bias in gene extraction on the basis of microarray gene-expression data", *Proc. Natl. Acad. Sci. U.S.A.*, 99(10):6562-6566 (2002).
Baggerly et al., "A comprehensive approach to the analysis of matrix-assisted laser desorption/ionization-time of flight proteomics spectra from serum samples", *Proteomics*, 3:1667-1672 (2003).
Ball et al., "An integrated approach utilizing artificial neural networks and SELDI mass spectrometry for the classification of human tumours and rapid identification of potential biomarkers", *Bioinformatics*, 18(3):395-404 (2002).
Becker et al., "Surfaced-enhanced laser desorption/ionization time-of-flight (SELDI-TOF) differentiation of serum protein profiles of BRCA-1 and sporadic breast cancer", *Ann. Surg. Oncol.*, 11(10):907-914 (2004).
Blackwell et al., "Plasma $_D$-dimer levels in operable breast cancer patients correlate with clinical stage and axillary lymph node status", *J. Clin. Oncol.*, 18(3):600-608 (2000).
Breiman, L., "Random Forests", *Machine Learning*, 45:5-32 (2001).
Carter et al., "Relation of tumor size, lymph node status, and survival in 24,740 breast cancer cases", *Cancer*; 63:181-187 (1989).
Chen et al., "Artificial neural networks analysis of surface-enhanced laser desorption/ionization mass spectra of serum protein pattern distinguishes colorectal cancer from healthy population", *Clin. Cancer Res.*, 10:8380-8385 (2004).
Coombes et al., "Quality control and peak finding for proteomics data collected from nipple aspirate fluid by surface-enhanced laser desorption and ionization", *Clin. Chem.*, 49(10):1615-1623 (2003).
Francis et al., "Endothelial cell responses to fibrin mediated by FPB cleavage and the amino terminus of the beta chain", *Blood Cells*, 19:291-306 (1993).
Gillette et al., "Place of pattern in proteomic biomarker discovery", *J. Proteome Res.*, 4:1143-1154 (2005).
Gray et al., "The mitogenic effects of the Bβ chain of fibrinogen are mediated through cell surface calreticulin", *J. Biol. Chem.*, 270(44):26602-26606 (1995).
Greiling et al., "Fibronectin provides a conduit for fibroblast transmigration from collagenous stroma into fibrin clot provisional matrix", *J. Cell Sci.*, 110(pt7):861-870 (1997).
Grizzle et al., "The Early Detection Research Network surface-enhanced laser desorption and ionization prostate cancer detection study: a study in biomarker validation in genitourinary oncology", *Urol. Oncol.*, 22:337-343 (2004).
Heer et al., "Serum Vascular Endothelial Growth Factor in Breast Cancer: Its Relation with Cancer Type and Estrogen Receptor Status", *J. Clin. Cancer Res.*, 7:3491-3494 (2001).
Karande et al., "Riboflavin carrier protein: a serum and tissue marker for breast carcinoma", *Int. J. Cancer*, 95:277-281 (2001).
Liotta et al., "Serum peptidome for cancer detection: spinning biologic trash into diagnostic gold", *J Clin. Invest.*, 116:26-30 (2006).
Liu et al., "Serum protein fingerprinting coupled with artificial neural network distinguishes glioma from healthy population or brain benign tumor", *J. Zhejiang Univ. Sci.*, 6B(1):4-10 (2005).
Mani et al., "Proteomic Data Analysis: Pattern Recognition for Medical Diagnosis and Biomarker Discovery", in *Next Generation of Data-Mining Applications*, Ch. 15, Kantardzic & Zurada, Eds., Wiley-IEEE Press, Piscataway, NJ, pp. 355-389 (2005).
Mattison et al., "Serum Proteins as Tumour Markers for Breast Cancer", *Br. J. Cancer*, 43(4):542-545 (1981).
Metz, C.E., "Basic principles of ROC analysis", *Semin Nucl. Med.*, 8:283-298 (1978).
Miller et al., "Canadian National Breast Screening Study: 1. Breast cancer detection and death rates among women aged 40 to 49 years", *Can. Med. Assoc. J.*, 147:1459-1476 (1992).
O'Marcaigh et al., "Estimating the Predictive Value of a Diagnostic Test, How to Prevent Misleading or Confusing Results", *Clin. Ped.*, 32(8):485-491 (1993).
O'Reilly et al., "Endostatin: an endogenous inhibitor of angiogenesis and tumor growth", *Cell*, 88:277-285 (1997).

(Continued)

*Primary Examiner* — Sean Aeder
(74) *Attorney, Agent, or Firm* — Mintz Levin Cohn Ferris Glovsky and Popeo, P.C.; Ivor R. Elrifi; Cynthia A. Kozakiewicz

(57) ABSTRACT

The present invention provides methods of detecting cancer using biomarkers.

15 Claims, 7 Drawing Sheets

OTHER PUBLICATIONS

Paweletz et al., "Proteomic patterns of nipple aspirate fluids obtained by SELDI-TOF: potential for new biomarkers to aid in the diagnosis of breast cancer", *Dis. Markers*, 17:301-307 (2001).

Perou et al., "Molecular portraits of human breast tumours", *Nature*, 406:747-752 (2000).

Petricoin et al., Use of proteomic patterns in serum to identify ovarian cancer, *Lancet*, 359:572-577 (2002).

Qu et al., "Boosted decision tree analysis of surface-enhanced laser desorption/ionization mass spectral serum profiles discriminates prostate cancer from noncancer patients", *Clin. Chem.*, 48(10):1835-1843 (2002).

Schnitt, S.J., "Traditional and Newer Pathologic Factors", *J. Natl. Cancer Inst. Monogr.*, 30:22-26 (2001).

Seibert et al., "Surface-enhanced laser desorption ionization time-of-flight mass spectrometry (SELDI TOF-MS) and ProteinChip® technology in proteomics research", *Pathol. Res. Pract.*, 200:83-94 (2004).

Seregni et al., "Circulating tumour markers in breast cancer", *Eur. J. Nucl. Med. Mol. Imaging*, 31(Suppl. 1):S15-S22 (2004).

Shultz, E.K., "Clinical Interpretation of Laboratory Procedures", in *Tietz Fundamentals of Clinical Chemistry*, Ch. 14, Burtis and Ashwood (Eds.), 4th Ed., W. B. Saunders Co., pp. 192-199 (1996).

Simpson-Haidaris, "Tumors and fibrinogen. The role of fibrinogen as an extracellular matrix protein", Ann. N.Y. Acad. Sci., 936:406-425 (2001).

Skogen et al., "Fibrinogen-derived peptide Bβ 1-42 is a multidomained neutrophil chemoattractant", *Blood*, 71(5):1475-1479 (1988).

Soltys et al., "The use of plasma surface-enhanced laser desorption/ionization time-of-flight mass spectrometry proteomic patterns for detection of head and neck squamous cell cancers", *Clin. Cancer Res.*, 10:4806-4812 (2004).

Sorlie et al., "Gene expression patterns of breast carcinomas distinguish tumor subclasses with clinical implications", *Proc. Natl. Acad. Sci. U.S.A.*, 98(19):10869-10874 (2001).

Sorlie et al., "Repeated observation of breast tumor subtypes in independent gene expression data sets", *Proc. Natl. Acad. Sci. U.S.A.*, 100(14):8418-8423 (2003).

Tang et al., "Current Developments in Seldi Affinity Technology", *Mass Spectrom. Rev.*, 23:34-44 (2004).

Thompson et al., "Fibrin degradation products in growth stimulatory extracts of pathological lesions", *Blood Coagul .Fibrinolysis*, 4:113-115 (1993).

Tolson et al., "Serum protein profiling by SELDI mass spectrometry: detection of multiple variants of serum amyloid alpha in renal cancer patients", *Lab. Invest.*, 84:845-856 (2004).

Valagussa et al., "Patterns of relapse and survival following radical mastectomy, Analysis of 716 consecutive patients", *Cancer*, 41:1170-1178 (1978).

Villanueva et al., "Correcting common errors in identifying cancer-specific serum peptide signatures", *J. Proteome Res.*, 4:1060-1072 (2005).

Villanueva et al., "Differential exoprotease activities confer tumor-specific serum peptidome patterns", *J. Clin. Invest.*, 116:271-284 (2006).

Villanueva et al., "Serum peptide profiling by magnetic particle-assisted, automated sample processing and MALDI-TOF mass spectrometry", *Anal. Chem.*, 76:1560-1570 (2004).

Vlahou et al., "A novel approach toward development of a rapid blood test for breast cancer", *Clin. Breast Cancer*, 4(3):203-209 (2003).

Wadsworth et al., "Serum protein profiles to identify head and neck cancer", *Clin. Cancer Res.*, 10:1625-1632 (2004).

Wang et al., "Loss of heterozygosity and its correlation with expression profiles in subclasses of invasive breast cancers", *Cancer Res.*, 64:64-71 (2004).

Wang et al., "Mass spectrometric analysis of protein markers for ovarian cancer", *Clin. Chem.*, 50(10):1939-1942 (2004).

Wilson et al., "Detection of differentially expressed proteins in early-stage melanoma patients using SELDI-TOF mass spectrometry", *Ann. N. Y. Acad. Sci.*, 1022:317-322 (2004).

Xiao et al., "Discovery of laryngeal carcinoma by serum proteomic pattern analysis", *Sci China C. Life Sci.*, 47(3):219-223 (2004).

Yarden et al., "Untangling the ErbB signalling network", *Nat. Rev. Mol. Cell Biol.*, 2:127-137 (2001).

Yasui et al., "A data-analytic strategy for protein biomarker discovery: profiling of high-dimensional proteomic data for cancer detection", *Biostatistics*, 4(3):449-463 (2003).

Ye et al., "Haptoglobin-α subunit as potential serum biomarker in ovarian cancer: identification and characterization using proteomic profiling and mass spectrometry", *Clin. Cancer Res.*, 9:2904-2911 (2003).

Yu et al., "An integrated approach to the detection of colorectal cancer utilizing proteomics and bioinformatics", *World J. Gastroenterol.*, 10(21):3127-3131 (2004).

Zhang et al., "Recursive SVM feature selection and sample classification for mass-spectrometry and microarray data", BMC Bioinformatics, 7:197 (2006) (Abstract Only).

Zhang et al., "Three biomarkers identified from serum proteomic analysis for the detection of early stage ovarian cancer", *Cancer Res.*, 64:5882-5890 (2004).

Zweig et al., "ROC Curve Analysis: An Example Showing the Relationships Among Serum Lipid and Apolipoprotein Concentrations in Identifying Patients With Coronary Artery Disease", *Clin. Chem.*, 38(8):1425-1428 (1992).

* cited by examiner

SEQUENCE LISTING

```
<160> NUMBER OF SEQ ID NOS: 6

<210> SEQ ID NO 1
<211> LENGTH: 25
<212> TYPE: PRT
<213> ORGANISM: Homo sapiens

<400> SEQUENCE: 1

Asp Glu Ala Gly Ser Glu Ala Asp His Glu Gly Thr His Ser Thr Lys
1               5                   10                  15

Arg Gly His Ala Lys Ser Arg Pro Val
            20                  25
```

```
<210> SEQ ID NO 2
<211> LENGTH: 866
<212> TYPE: PRT
<213> ORGANISM: Homo sapiens

<400> SEQUENCE: 2

Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20                  25                  30

Gly Val Arg Gly Pro Arg Val Val Glu Arg His Gln Ser Ala Cys Lys
        35                  40                  45

Asp Ser Asp Trp Pro Phe Cys Ser Asp Glu Asp Trp Asn Tyr Lys Cys
    50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
    130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
    210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
        275                 280                 285

Pro Ser Ser Ala Gly Ser Trp Asn Ser Gly Ser Ser Gly Pro Gly Ser
    290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
            340                 345                 350

Arg Pro Gly Ser Thr Gly Thr Trp Asn Pro Gly Ser Ser Glu Arg Gly
        355                 360                 365

Ser Ala Gly His Trp Thr Ser Glu Ser Ser Val Ser Gly Ser Thr Gly
    370                 375                 380

Gln Trp His Ser Glu Ser Gly Ser Phe Arg Pro Asp Ser Pro Gly Ser
```

-continued

```
              385                 390                 395                 400
        Gly Asn Ala Arg Pro Asn Asn Pro Asp Trp Gly Thr Phe Glu Glu Val
                            405                 410                 415

Ser Gly Asn Val Ser Pro Gly Thr Arg Arg Glu Tyr His Thr Glu Lys
                    420                 425                 430

Leu Val Thr Ser Lys Gly Asp Lys Glu Leu Arg Thr Gly Lys Glu Lys
                        435                 440                 445

Val Thr Ser Gly Ser Thr Thr Thr Arg Arg Ser Cys Ser Lys Thr
                450                 455                 460

Val Thr Lys Thr Val Ile Gly Pro Asp Gly His Lys Glu Val Thr Lys
        465                 470                 475                 480

Glu Val Val Thr Ser Glu Asp Gly Ser Asp Cys Pro Glu Ala Met Asp
                        485                 490                 495

Leu Gly Thr Leu Ser Gly Ile Gly Thr Leu Asp Gly Phe Arg His Arg
                    500                 505                 510

His Pro Asp Glu Ala Ala Phe Phe Asp Thr Ala Ser Thr Gly Lys Thr
                        515                 520                 525

Phe Pro Gly Phe Phe Ser Pro Met Leu Gly Glu Phe Val Ser Glu Thr
                    530                 535                 540

Glu Ser Arg Gly Ser Glu Ser Gly Ile Phe Thr Asn Thr Lys Glu Ser
        545                 550                 555                 560

Ser Ser His His Pro Gly Ile Ala Glu Phe Pro Ser Arg Gly Lys Ser
                            565                 570                 575

Ser Ser Tyr Ser Lys Gln Phe Thr Ser Ser Thr Ser Tyr Asn Arg Gly
                        580                 585                 590

Asp Ser Thr Phe Glu Ser Lys Ser Tyr Lys Met Ala Asp Glu Ala Gly
                    595                 600                 605

Ser Glu Ala Asp His Glu Gly Thr His Ser Thr Lys Arg Gly His Ala
                610                 615                 620

Lys Ser Arg Pro Val Arg Asp Cys Asp Asp Val Leu Gln Thr His Pro
        625                 630                 635                 640

Ser Gly Thr Gln Ser Gly Ile Phe Asn Ile Lys Leu Pro Gly Ser Ser
                            645                 650                 655

Lys Ile Phe Ser Val Tyr Cys Asp Gln Glu Thr Ser Leu Gly Gly Trp
                        660                 665                 670

Leu Leu Ile Gln Gln Arg Met Asp Gly Ser Leu Asn Phe Asn Arg Thr
                    675                 680                 685

Trp Gln Asp Tyr Lys Arg Gly Phe Gly Ser Leu Asn Asp Glu Gly Glu
                690                 695                 700

Gly Glu Phe Trp Leu Gly Asn Asp Tyr Leu His Leu Leu Thr Gln Arg
        705                 710                 715                 720

Gly Ser Val Leu Arg Val Glu Leu Glu Asp Trp Ala Gly Asn Glu Ala
                            725                 730                 735

Tyr Ala Glu Tyr His Phe Arg Val Gly Ser Glu Ala Glu Gly Tyr Ala
                        740                 745                 750

Leu Gln Val Ser Ser Tyr Glu Gly Thr Ala Gly Asp Ala Leu Ile Glu
                    755                 760                 765

Gly Ser Val Glu Glu Gly Ala Glu Tyr Thr Ser His Asn Asn Met Gln
                770                 775                 780

Phe Ser Thr Phe Asp Arg Asp Ala Asp Gln Trp Glu Glu Asn Cys Ala
        785                 790                 795                 800

Glu Val Tyr Gly Gly Gly Trp Trp Tyr Asn Asn Cys Gln Ala Ala Asn
                            805                 810                 815
```

```
Leu Asn Gly Ile Tyr Tyr Pro Gly Gly Ser Tyr Asp Pro Arg Asn Asn
                820                 825                 830

Ser Pro Tyr Glu Ile Glu Asn Gly Val Val Trp Val Ser Phe Arg Gly
                835                 840                 845

Ala Asp Tyr Ser Leu Arg Ala Val Arg Met Lys Ile Arg Pro Leu Val
                850                 855                 860

Thr Gln
865

<210> SEQ ID NO 3
<211> LENGTH: 410
<212> TYPE: PRT
<213> ORGANISM: Homo sapiens

<400> SEQUENCE: 3

His Leu Pro Leu Ile Lys Met Lys Pro Val Pro Asp Leu Val Pro Gly
  1               5                  10                  15

Asn Phe Lys Ser Gln Leu Gln Lys Val Pro Pro Glu Trp Lys Ala Leu
                 20                  25                  30

Thr Asp Met Pro Gln Met Arg Met Glu Leu Glu Arg Pro Gly Gly Asn
                 35                  40                  45

Glu Ile Thr Arg Gly Gly Ser Thr Ser Tyr Gly Thr Gly Ser Glu Thr
 50                  55                  60

Glu Ser Pro Arg Asn Pro Ser Ser Ala Gly Ser Trp Asn Ser Gly Ser
 65                  70                  75                  80

Ser Gly Pro Gly Ser Thr Gly Asn Arg Asn Pro Gly Ser Ser Gly Thr
                 85                  90                  95

Gly Gly Thr Ala Thr Trp Lys Pro Gly Ser Ser Gly Pro Gly Ser Thr
                100                 105                 110

Gly Ser Trp Asn Ser Gly Ser Ser Gly Thr Gly Ser Thr Gly Asn Gln
                115                 120                 125

Asn Pro Gly Ser Pro Arg Pro Gly Ser Thr Gly Thr Trp Asn Pro Gly
                130                 135                 140

Ser Ser Glu Arg Gly Ser Ala Gly His Trp Thr Ser Glu Ser Ser Val
145                 150                 155                 160

Ser Gly Ser Thr Gly Gln Trp His Ser Glu Ser Gly Ser Phe Arg Pro
                165                 170                 175

Asp Ser Pro Gly Ser Gly Asn Ala Arg Pro Asn Asn Pro Asp Trp Gly
                180                 185                 190

Thr Phe Glu Glu Val Ser Gly Asn Val Ser Pro Gly Thr Arg Arg Glu
                195                 200                 205

Tyr His Thr Glu Lys Leu Val Thr Ser Lys Gly Asp Lys Glu Leu Arg
                210                 215                 220

Thr Gly Lys Glu Lys Val Thr Ser Gly Ser Thr Thr Thr Arg Arg
225                 230                 235                 240

Ser Cys Ser Lys Thr Val Thr Lys Thr Val Ile Gly Pro Asp Gly His
                245                 250                 255

Lys Glu Val Thr Lys Glu Val Val Thr Ser Glu Asp Gly Ser Asp Cys
                260                 265                 270

Pro Glu Ala Met Asp Leu Gly Thr Leu Ser Gly Ile Gly Thr Leu Asp
                275                 280                 285

Gly Phe Arg His Arg His Pro Asp Glu Ala Ala Phe Phe Asp Thr Ala
                290                 295                 300

Ser Thr Gly Lys Thr Phe Pro Gly Phe Phe Ser Pro Met Leu Gly Glu
305                 310                 315                 320
```

```
Phe Val Ser Glu Thr Glu Ser Arg Gly Ser Glu Ser Gly Ile Phe Thr
            325                 330                 335

Asn Thr Lys Glu Ser Ser His His Pro Gly Ile Ala Glu Phe Pro
            340                 345                 350

Ser Arg Gly Lys Ser Ser Tyr Ser Lys Gln Phe Thr Ser Ser Thr
            355                 360                 365

Ser Tyr Asn Arg Gly Asp Ser Thr Phe Glu Ser Lys Ser Tyr Lys Met
        370                 375                 380

Ala Asp Glu Ala Gly Ser Glu Ala Asp His Glu Gly Thr His Ser Thr
385                 390                 395                 400

Lys Arg Gly His Ala Lys Ser Arg Pro Val
            405                 410

<210> SEQ ID NO 4
<211> LENGTH: 141
<212> TYPE: PRT
<213> ORGANISM: Homo sapiens

<400> SEQUENCE: 4

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140

<210> SEQ ID NO 5
<211> LENGTH: 146
<212> TYPE: PRT
<213> ORGANISM: Homo sapiens

<400> SEQUENCE: 5

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
```

```
                100             105             110
Val Leu Ala His His Phe Gly Lys Glu Phe Thr Pro Pro Val Gln Ala
        115                 120                 125
Ala Tyr Gln Lys Val Val Ala Gly Val Ala Asn Ala Leu Ala His Lys
        130                 135                 140
Tyr His
145

<210> SEQ ID NO 6
<211> LENGTH: 847
<212> TYPE: PRT
<213> ORGANISM: Homo sapiens

<400> SEQUENCE: 6

Ala Asp Ser Gly Glu Gly Asp Phe Leu Ala Glu Gly Gly Gly Val Arg
1               5                   10                  15
Gly Pro Arg Val Val Glu Arg His Gln Ser Ala Cys Lys Asp Ser Asp
            20                  25                  30
Trp Pro Phe Cys Ser Asp Glu Asp Trp Asn Tyr Lys Cys Pro Ser Gly
        35                  40                  45
Cys Arg Met Lys Gly Leu Ile Asp Glu Val Asn Gln Asp Phe Thr Asn
    50                  55                  60
Arg Ile Asn Lys Leu Lys Asn Ser Leu Phe Glu Tyr Gln Lys Asn Asn
65                  70                  75                  80
Lys Asp Ser His Ser Leu Thr Thr Asn Ile Met Glu Ile Leu Arg Gly
                85                  90                  95
Asp Phe Ser Ser Ala Asn Asn Arg Asp Asn Thr Tyr Asn Arg Val Ser
            100                 105                 110
Glu Asp Leu Arg Ser Arg Ile Glu Val Leu Lys Arg Lys Val Ile Glu
        115                 120                 125
Lys Val Gln His Ile Gln Leu Leu Gln Lys Asn Val Arg Ala Gln Leu
    130                 135                 140
Val Asp Met Lys Arg Leu Glu Val Asp Ile Asp Ile Lys Ile Arg Ser
145                 150                 155                 160
Cys Arg Gly Ser Cys Ser Arg Ala Leu Ala Arg Glu Val Asp Leu Lys
                165                 170                 175
Asp Tyr Glu Asp Gln Gln Lys Gln Leu Glu Gln Val Ile Ala Lys Asp
            180                 185                 190
Leu Leu Pro Ser Arg Asp Arg Gln His Leu Pro Leu Ile Lys Met Lys
        195                 200                 205
Pro Val Pro Asp Leu Val Pro Gly Asn Phe Lys Ser Gln Leu Gln Lys
    210                 215                 220
Val Pro Pro Glu Trp Lys Ala Leu Thr Asp Met Pro Gln Met Arg Met
225                 230                 235                 240
Glu Leu Glu Arg Pro Gly Gly Asn Glu Ile Thr Arg Gly Gly Ser Thr
                245                 250                 255
Ser Tyr Gly Thr Gly Ser Glu Thr Glu Ser Pro Arg Asn Pro Ser Ser
            260                 265                 270
Ala Gly Ser Trp Asn Ser Gly Ser Ser Gly Pro Gly Ser Thr Gly Asn
        275                 280                 285
Arg Asn Pro Gly Ser Ser Gly Thr Gly Gly Thr Ala Thr Trp Lys Pro
    290                 295                 300
Gly Ser Ser Gly Pro Gly Ser Thr Gly Ser Trp Asn Ser Gly Ser Ser
305                 310                 315                 320
Gly Thr Gly Ser Thr Gly Asn Gln Asn Pro Gly Ser Pro Arg Pro Gly
```

```
                    325                 330                 335
Ser Thr Gly Thr Trp Asn Pro Gly Ser Ser Glu Arg Gly Ser Ala Gly
                340                 345                 350

His Trp Thr Ser Glu Ser Ser Val Ser Gly Ser Thr Gly Gln Trp His
                355                 360                 365

Ser Glu Ser Gly Ser Phe Arg Pro Asp Ser Pro Gly Ser Gly Asn Ala
    370                 375                 380

Arg Pro Asn Asn Pro Asp Trp Gly Thr Phe Glu Val Ser Gly Asn
385                 390                 395                 400

Val Ser Pro Gly Thr Arg Arg Glu Tyr His Thr Glu Lys Leu Val Thr
                405                 410                 415

Ser Lys Gly Asp Lys Glu Leu Arg Thr Gly Lys Glu Lys Val Thr Ser
                420                 425                 430

Gly Ser Thr Thr Thr Arg Arg Ser Cys Ser Lys Thr Val Thr Lys
                435                 440                 445

Thr Val Ile Gly Pro Asp Gly His Lys Glu Val Thr Lys Glu Val Val
                450                 455                 460

Thr Ser Glu Asp Gly Ser Asp Cys Pro Glu Ala Met Asp Leu Gly Thr
465                 470                 475                 480

Leu Ser Gly Ile Gly Thr Leu Asp Gly Phe Arg His Arg His Pro Asp
                485                 490                 495

Glu Ala Ala Phe Phe Asp Thr Ala Ser Thr Gly Lys Thr Phe Pro Gly
                500                 505                 510

Phe Phe Ser Pro Met Leu Gly Glu Phe Val Ser Glu Thr Glu Ser Arg
                515                 520                 525

Gly Ser Glu Ser Gly Ile Phe Thr Asn Thr Lys Glu Ser Ser Ser His
                530                 535                 540

His Pro Gly Ile Ala Glu Phe Pro Ser Arg Gly Lys Ser Ser Ser Tyr
545                 550                 555                 560

Ser Lys Gln Phe Thr Ser Ser Thr Ser Tyr Asn Arg Gly Asp Ser Thr
                565                 570                 575

Phe Glu Ser Lys Ser Tyr Lys Met Ala Asp Glu Ala Gly Ser Glu Ala
                580                 585                 590

Asp His Glu Gly Thr His Ser Thr Lys Arg Gly His Ala Lys Ser Arg
                595                 600                 605

Pro Val Arg Asp Cys Asp Asp Val Leu Gln Thr His Pro Ser Gly Thr
                610                 615                 620

Gln Ser Gly Ile Phe Asn Ile Lys Leu Pro Gly Ser Ser Lys Ile Phe
625                 630                 635                 640

Ser Val Tyr Cys Asp Gln Glu Thr Ser Leu Gly Gly Trp Leu Leu Ile
                645                 650                 655

Gln Gln Arg Met Asp Gly Ser Leu Asn Phe Asn Arg Thr Trp Gln Asp
                660                 665                 670

Tyr Lys Arg Gly Phe Gly Ser Leu Asn Asp Glu Gly Glu Gly Glu Phe
                675                 680                 685

Trp Leu Gly Asn Asp Tyr Leu His Leu Leu Thr Gln Arg Gly Ser Val
                690                 695                 700

Leu Arg Val Glu Leu Glu Asp Trp Ala Gly Asn Glu Ala Tyr Ala Glu
705                 710                 715                 720

Tyr His Phe Arg Val Gly Ser Glu Ala Glu Gly Tyr Ala Leu Gln Val
                725                 730                 735

Ser Ser Tyr Glu Gly Thr Ala Gly Asp Ala Leu Ile Glu Gly Ser Val
                740                 745                 750
```

-continued

```
Glu Glu Gly Ala Glu Tyr Thr Ser His Asn Asn Met Gln Phe Ser Thr
        755             760             765

Phe Asp Arg Asp Ala Asp Gln Trp Glu Glu Asn Cys Ala Glu Val Tyr
    770             775                 780

Gly Gly Gly Trp Trp Tyr Asn Asn Cys Gln Ala Ala Asn Leu Asn Gly
785             790             795                     800

Ile Tyr Tyr Pro Gly Gly Ser Tyr Asp Pro Arg Asn Asn Ser Pro Tyr
            805             810                     815

Glu Ile Glu Asn Gly Val Val Trp Val Ser Phe Arg Gly Ala Asp Tyr
            820             825             830

Ser Leu Arg Ala Val Arg Met Lys Ile Arg Pro Leu Val Thr Gln
        835             840             845
```

FIBRINOGEN ALPHA AND HEMOGLOBIN POLYPEPTIDES AS CANCER MARKERS

RELATED APPLICATIONS

This application is a continuation application of U.S. Ser. No. 11/920,494, filed Nov. 16, 2007, which is a national stage application, filed under 35 U.S.C. §371, of International Application No. PCT/US2006/019124, filed on May 16, 2006 which claims the benefit of U.S. Ser. No. 60/681,508, filed May 16, 2005.

FIELD OF THE INVENTION

The invention relates to generally to detecting cancer using a biomarker.

BACKGROUND OF THE INVENTION

Breast cancer is a common disease, with one in eight women affected by the age of 85. It strikes more than 200,000 women each year; and 44,000 of these women will die of their disease[1]. There is a compelling need to diagnose and treat breast cancer more effectively. Moreover, earlier disease stage at diagnosis correlates directly with improved survival[1]. Local and systemic treatments cure a substantial proportion of early-stage patients[2,3]. Hence, improvements in screening and early detection will unequivocally save lives.

Breast cancer is a heterogeneous disease, with several phenotypic distinctions and with an unpredictable clinical course[4-6]. Molecular markers are used to define subsets of tumors. Useful classification is achieved by determination of the estrogen receptor, progesterone receptor, and HER2 content of cancer cells[7,8]. Recently, finer classification was performed using genome-wide RNA expression arrays[9]. In general, HER2-positive tumors segregate in a unique subset of human breast cancers, substantiating the importance of this oncogenic protein. A clinically useful classification divides breast cancer into hormone receptor positive tumors, HER2 positive tumors and tumors negative for both markers. These clinical distinctions are important for treatment response, and it is likely they effect identification of sensitive and specific diagnostic biomarkers as well.

Currently screening mammography is the mainstay for breast cancer detection. However, at least 10% of breast cancers cannot be visualized with mammography because they do not create a change in the density or architecture of breast tissue[10]. Only marginal benefits are demonstrated in woman under age 50 subjected to annual screening mammography[10]. To complement screening with mammography, there are few serum markers of any clinical utility in breast cancer and none that are useful for early detection. Markers used in clinical practice (such as CEA, CA 15.3) reflect tumor burden and are useful for addressing questions of response to therapy rather than diagnosis[11]. Other markers have been evaluated,[12,13] but lack the sensitivity and specificity to serve as diagnostic biomarkers for breast cancer. There is a need for a broader-based approach to biomarker discovery and tests that will complement mammography.

SUMMARY OF THE INVENTION

The invention provides biological markers to monitor the diagnosis and prognosis of cancer.

Cancers are diagnosed in a subject by detecting a fibrinogen αC domain peptide or a hemoglobin polypeptide in a sample obtained from the subject. A decrease (i.e. lower level) in the amount of the fibrinogen αC domain peptide in the sample compared to a normal control sample (e.g., a control value) indicates of the presence of a cancer in the subject. Whereas, a similarity or an increase in the amount of the fibrinogen αC domain peptide indicates the absence of a cancer in the subject. An increase (i.e. higher level) in the amount of the hemoglobin polypeptide in the sample compared to a normal control sample (e.g., a control value) indicates of the presence of a cancer in the subject. Whereas, a similarity or a decrease in the amount of the hemoglobin polypeptide indicates the absence of a cancer in the subject. By lower level is meant at least a 2, 4, 5, 10-fold or lower value in the test sample compared to the control sample.

The progression of a cancer is monitored by detecting a fibrinogen αC domain peptide or a hemoglobin polypeptide in a two or more samples obtained from a subject over time and comparing the amount of fibrinogen αC domain peptide or a hemoglobin polypeptide detected. For example, a first sample is obtained prior to the subject receiving treatment and one or more subsequent samples are taken after or during treatment of the subject. The cancer is progressing if the amount of the fibrinogen αC domain peptide decrease over time or the amount of hemoglobin increases over time. Whereas the cancer is not progressing in the amount of the fibrinogen αC domain peptide polypeptide remains constant or increase over time or the hemoglobin polypeptide remains constant or decreased over time.

The sample is a biological sample obtained from the subject. The sample is for example, serum, blood plasma, ascites fluid, or urine.

A full-length fibrinogen αC domain peptide is detected. Alternatively, a fragment of the fibrinogen αC domain peptide is detected. For example, a fibrinogen αC domain peptide containing amino acid residues 605 to 629 of a fibrinogen alpha polypeptide when numbered in accordance with a mature wild type fibrinogen polypeptide (e.g., Swiss Protein Accession Number P02671) is detected. An exemplary fibrinogen αC domain peptide includes the amino acid sequence of SEQ ID NO:1 or a amino acid sequence at least 95%, 96%, 97%, 98% or 99% identical to the amino acid sequence of SEQ ID NO:1. Preferably, the fibrinogen αC domain peptide contains at least 5, 10, 15, 20 contiguous amino acid residues of SEQ ID NO:1. The fibrinogen αC domain peptide or hemoglobin polypeptide is detected by any means known in the art. The fibrinogen αC domain peptide or hemoglobin polypeptide is detected electrophoretically or immuno chemically. Immunochemical detection includes for example, radio-immunoassay, immunofluorescence assay, or enzyme-linked immunosorbant assay. For example, a fibrinogen αC domain peptide is detected using an anti-fibrinogen αC domain peptide antibody, and the amount of antigen-antibody complex is detected as a measure of the fibrinogen αC domain peptide in the sample.

Cancers include solid tumors (e.g., breast cancer, colon cancer, liver cancer, pancreatic cancer, ovarian cancer, prostate cancer, or lung cancer) or liquid tumors (e.g., lymphoma or leukemia)

Optionally, the method is carried out on a subject concurrently with testing that patient for elevated Alpha-fetoprotein (AFP), Beta-2-microglobulin (B2M), Bladder tumor antigen (BTA), CA 15-3, CA 27.29, CA 125, CA 72-4, CA 19-9, Calcitonin, Carcinoembryonic antigen (CEA), Chromogranin A, Serum gamma globulin, Serum Her-2/neu, Human chorionic gonadotropin (HCG), Lipid Associated Sialic Acid in Plasma (LASA-P), NMP22, Neuron-specific enolase (NSE), Prostate-specific antigen (PSA), Prostatic acid phosphatase (PAP), Prostate-specific membrane antigen (PSMA), S-100, TA-90, Thyroglobulin, or Tissue polypeptide antigen (TPA) levels, with the combined results providing a superior indication of the presence of cancer than screening or monitoring with a fibrinogen αC domain peptide alone. Additionally, a peptide with mass to charge (m/z) ratio of about 7558, 7933, 1418 or 15168 is also detected.

The subject has not been previously diagnosed as having cancer. Alternatively, the subject has been diagnosed with cancer. Optionally, the subject has been previously treated surgically or hormonally for cancer. The subject may be geneticallt at risk for breast cancer and/or is positive for the BRAC1 or BRAC2 gene.

Kits containing in one or more containers, a fibrinogen αC domain peptide antibody or a hemoglobin polypeptide, a detection reagent and instructions are further provides by the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1A:
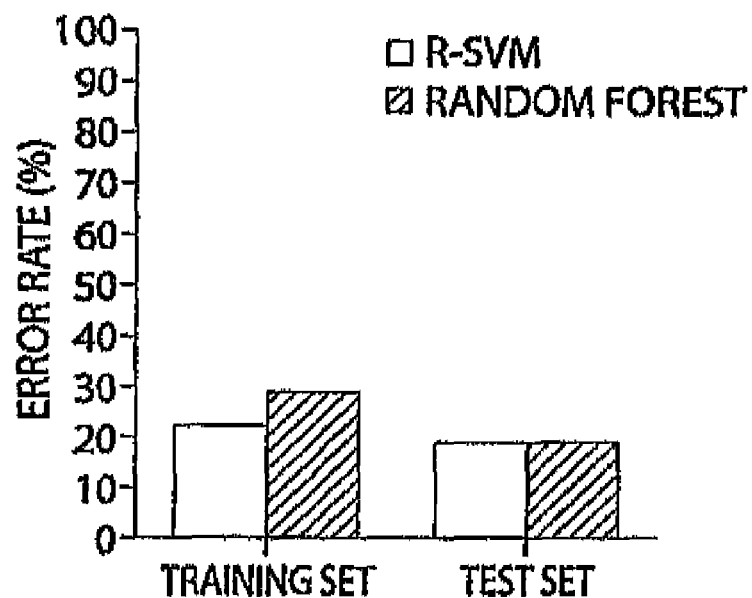
FIG. 1A is a bar chart showing the error rate of both R-SVM and random forest selected biomarker sets. The external cross validation error rate (i.e., the cross-validation error rate was estimated by leaving sample(s) out prior to feature selection, so that to guarantee an unbiased CV error estimation) was estimated on the training data set by each algorithm. The same model was then applied on the test data set and the prediction error was shown.

The invention is based upon the discovery of biomarkers for the detection of cancer. Using Surface Enhanced Laser Desorption and Ionization (SELDI) technology, protein biomarkers were identified in plasma that was differentially expressed in control versus cancer plasma samples. One marker, which has a mass to charge (m/z) of about 2660 and was further identified as a COOH terminal fragment of fibrinogen alpha (referred to herein as the fibrinogen αC domain peptide) reverted toward control levels following surgical treatment. Other peptide biomarkers useful in the detection of cancer include peptides with mass to charge (m/z) ratio of about 7558, 7933, 1418, 15876 or 15168. The peptide with the m/z ratio of about 7558 was identified as doubly charged alpha globulin, the peptide with the m/z ratio of about 7933 was identified as double charged beta globulin; the peptide with the m/z ratio of about 15168 was identified as alpha globulin; the peptide with the m/z ratio of about 15876 was identified as beta globulin. Thus, the fibrinogen αC domain peptide and hemoglobin are ideal candidate markers of cancer. Accordingly, the invention provides methods of detecting and evaluating cancer in a subject by measuring the levels of fibrinogen αC domain peptide or a hemoglobin polypeptide. In addition to measuring the biomarker fragments, full length polypeptides or the protease that cleave the full length polypeptides to the biomarker peptides can also be measured (e.g., detected)

The methods disclosed herein are employed with subjects suspected of carrying cancer, to monitor subjects who have been previously diagnosed as carrying cancer, to monitor subjects who have been treated for cancer and to screen subjects who have not been previously diagnosed as carrying cancer.

Human fibrinogen is a circulating 340 kDa glycoprotein that is comprised of two symmetric half molecules, each consisting of one set of three different polypeptide chains termed α, β and γ, and is synthesized by the liver. The concentration of circulating fibrinogen is about 9 µM in normal blood. At sites of tissue injury, fibrinogen is converted to fibrin by a-thrombin to form a fibrin clot. This fibrin clot is subsequently degraded into a number of fragments, primarily by plasmin. Many of those degradation fragments have biological functions, such as mitogenic effects on fibroblast and endothelial cells, vasoactive effects, and migratory effects. In tumors, fibrinogen is characterized as protumorigenic because it binds growth factors such as VEGF, promotes endothelial cell proliferation, interacts with other matrix proteins providing a physical protective barrier, and serves as a scaffold for cell migration via integrin binding. However, there is also evidence suggesting that fibrinogen can also be antitumorigenic by inhibiting cell motility due to its adhesive properties and by acting as a chemoattractant for inflammatory cell infiltration in the immune response.

By a fibrinogen αC domain peptide is meant that the peptide contains a portion of the COOH terminus of a fibrinogen alpha peptide, e.g., amino acids 220-629 (SEQ ID NO:3). No particular length is implied by the term "peptide." The fibrinogen αC domain peptide is less than 390 amino acids in length, e.g., less than or equal to 150, 100, 75, 50, 35, 26, 25, 15, or 10 amino acids in length. Preferably, a fibrinogen αC domain peptide includes amino acids 605-629 when numbered in accordance with a full length mature wild type fibrinogen alphapeptide. An exemplary fibrinogen αC domain peptide includes a peptide, which includes (in whole or in part) the sequence $NH_2$-DEAGSEADHEGTHST-KRGHAKSRPV-$COOH$ (SEQ ID NO:1). Preferably, the fibrinogen αC domain peptide includes at least 5, 10, 15, 20 or more contiguous amino acids of SEQ ID NO:1.

A wild type unprocessed fibrinogen alpha polypeptide is shown in Table A (SEQ ID NO:2). The mature (i.e., processed) fibrinogen alpha peptide is underlined (amino acids 20-866; SEQ ID NO:6); the αC domain is shown in bold.

TABLE A (SEQ ID NO: 2)
Human Fibrinogen Alpha

|  | 10 | 20 | 30 | 40 | 50 | 60 |
|---|---|---|---|---|---|---|
|  | MFSMRIVCLV | LSVVGTAWTA | DSGEGDFLAE | GGGVRGPRVV | ERHQSACKDS | DWPFCSDEDW |
|  | 70 | 80 | 90 | 100 | 110 | 120 |
|  | NYKCPSGCRM | KGLIDEVNQD | FTNRINKLKN | SLFEYQKNNK | DSHSLTTNIM | EILRGDFSSA |
|  | 130 | 140 | 150 | 160 | 170 | 180 |
|  | NNRDNTYNRV | SEDLRSRIEV | LKRKVIEKVQ | HIQLLQKNVR | AQLVDMKRLE | VDIDIKIRSC |
|  | 190 | 200 | 210 | 220 | 230 | 240 |
|  | RGSCSRALAR | EVDLKDYEDQ | QKQLEQVIAK | DLLPSRDRQH | LPLIKMKPVP | DLVPGNFKSQ |
|  | 250 | 260 | 270 | 280 | 290 | 300 |
|  | LQKVPPEWKA | LTDMPQMRME | LERPGGNEIT | RGGSTSYGTG | SETESPRNPS | SAGSWNSGSS |
|  | 310 | 320 | 330 | 340 | 350 | 360 |
|  | GPGSTGNRNP | GSSGTGGTAT | WKPGSSGPGS | TGSWNSGSSG | TGSTGNQNPG | SPRPGSTGTW |
|  | 370 | 380 | 390 | 400 | 410 | 420 |
|  | NPGSSERGSA | GHWTSESSVS | GSTGQWHSES | GSFRPDSPGS | GNARPNNPDW | GTFEEVSGNV |
|  | 430 | 440 | 450 | 460 | 470 | 480 |
|  | SPGTRREYHT | EKLVTSKGDK | ELRTGKEKVT | SGSTTTTRRS | CSKTVTKTVI | GPDGHKEVTK |
|  | 490 | 500 | 510 | 520 | 530 | 540 |
|  | EVVTSEDGSD | CPEAMDLGTL | SGIGTLDGFR | HRHPDEAAFF | DTASTGKTFP | GFFSPMLGEF |
|  | 550 | 560 | 570 | 580 | 590 | 600 |
|  | VSETESRGSE | SGIFTNTKES | SSHHPGIAEF | PSRGKSSSYS | KQFTSSTSYN | RGDSTFESKS |
|  | 610 | 620 | 630 | 640 | 650 | 660 |
|  | YKMADEAGSE | ADHEGTHSTK | RGHAKSRPVR | DCDDVLQTHP | SGTQSGIFNI | KLPGSSKIFS |
|  | 670 | 680 | 690 | 700 | 710 | 720 |
|  | VYCDQETSLG | GWLLIQQRMD | GSLNFNRTWQ | DYKRGFGSLN | DEGEGEFWLG | NDYLHLLTQR |
|  | 730 | 740 | 750 | 760 | 770 | 780 |
|  | GSVLRVELED | WAGNEAYAEY | HFRVGSEAEG | YALQVSSYEG | TAGDALIEGS | VEEGAEYTSH |

TABLE A-continued (SEQ ID NO: 2)
Human Fibrinogen Alpha

```
        790        800        810        820        830        840
NNMQFSTFDR DADQWEENCA EVYGGGWWYN NCQAANLNGI YYPGGSYDPR NNSPYEIENG 850        860
VVWVSFRGAD YSLRAVRMKI RPLVTQ
```

Hemoglobin is the protein molecule in red blood cells, which carries oxygen from the lungs to the body's tissues and returns carbon dioxide from the tissues to the lungs. The iron contained in hemoglobin is responsible for the red color of blood. Hemoglobin is a tetrameric molecule. Each hemoglobin tetramer consists of 2 alpha and 2 beta globin subunits. Each alpha globin subunit consists of 141 amino acids, and has a molecular weight of 15,126 Daltons. Each beta globin subunit consists of 146 amino acids, and has a molecular weight of 15,867 Daltons.

The normal ranges for hemoglobin depend on the age and, beginning in adolescence, the sex of the person. The normal ranges are: Newborns: 17-22 gm/dl; One (1) week of age: 15-20 gm/dl; One (1) month of age: 11-15 gm/dl; Children: 11-13 gm/dl; Adult males: 14-18 gm/dl; Adult women: 12-16 gm/dl; Men after middle age: 12.4-14.9 gm/dl; Women after middle age: 11.7-13.8 gm/dl.

By a hemoglobin polypeptide is meant an alpha globin polypeptide or fragment thereof, a beta globulin polypeptide or fragment thereof, dimers or tetramers of an alpha and beta globulin polypeptide or fragment thereof. An alpha globin polypeptide is shown in Table B (SEQ ID NO:4) and beta globin polypeptide is shown in Table C (SEQ ID NO:5)

TABLE B (SEQ ID NO: 4)
Human Alpha Globin

```
        10         20         30         40         50         60
VLSPADKTNV KAAWGKVGAH AGEYGAEALE RMFLSFPTTK TYFPHFDLSH GSAQVKGHGK 70         80         90        100        110        120
KVADALTNAV AHVDDMPNAL SALSDLHAHK LRVDPVNFKL LSHCLLVTLA AHLPAEFTPA 130        140
VHASLDKFLA SVSTVLTSKY R
```

TABLE C (SEQ ID NO: 5)
Human Beta Globin

```
        10         20         30         40         50         60
VHLTPEEKSA VTALWGKVNV DEVGGEALGR LLVVYPWTQR FFESFGDLST PDAVMGNPKV 70         80         90        100        110        120
KAHGKKVLGA FSDGLAHLDN LKGTFATLSE LHCDKLHVDP ENFRLLGNVL VCVLAHHFGK 130        140
EFTPPVQAAY QKVVAGVANA LAHKYH
```

Diagnostic and Prognostic Methods

Cancers are detected by examining the amount of fibrinogen αC domain peptide or a hemoglobin polypeptide in a test sample (i.e., a patient derived sample). A change in the level if the fibrinogen αC domain peptide or a hemoglobin polypeptide compared to a control sample is indicative of cancer in the subject. The change may be an increase or a decrease in the fibrinogen αC domain peptide or a hemoglobin polypeptide relative to a control sample. The control sample is prepared (i.e., fractionated) in a similar fashion as the test sample.

Optionally, full length fibrinogen or the protease activity that produces the fibrinogen αC domain peptide is detected. The cancer is a solid tumor such as for example, breast cancer, ovarian cancer, endocervical cancer, fallopian cancer, uterine cancer, prostate cancer, liver cancer, lung cancer, pancreatic cancer, stomach cancer, or colorectal cancer. Alternatively, the cancer is a liquid tumor such as leukemia or lymphoma. A sample is for example, blood, serum, acsites fluid, urine, or other bodily fluids.

The amount of the fibrinogen αC domain peptide or hemoglobin polypeptide is determined in the test sample and compared to the expression of the normal control level. By normal control level is meant the expression level of a fibrinogen αC domain peptide or hemoglobin polypeptide typically found in a subject not suffering from a cancer. A decrease of the level in the patient derived sample of a fibrinogen αC domain peptide indicates that the subject is suffering from or is at risk of developing cancer. In contrast, when the methods are applied prophylacticly, a similar level or an increase in the level in the patient derived sample of a fibrinogen αC domain peptide indicates that the subject is not suffering from or is at risk of developing cancer. An increase of the level in the patient derived sample of a hemoglobin polypeptide indicates that the subject is suffering from or is at risk of developing cancer. In contrast, when the methods are applied prophylactically, a similar level or a decrease in the level in the patient derived sample of a hemoglobin polypeptide indicates that the subject is not suffering from or is at risk of developing cancer.

The alteration in the amount of the fibrinogen αC domain peptide or hemoglobin polypeptide is statistically significant. By statistically significant is meant that the alteration is greater than what might be expected to happen by change alone. Statistical significance is determined by method known in the art. For example statistical significance is determined by p-value. The p-values is a measure of probability that a difference between groups during an experiment happened by chance. ($P(z \geq z_{observed})$). For example, a p-value of 0.01 means that there is a 1 in 100 chance the result occurred by chance. The lower the p-value, the more likely it is that the difference between groups was caused by treatment. An alteration is statistically significant if the p-value is at least 0.05. Preferably, the p-value is 0.04, 0.03, 0.02, 0.01, 0.005, 0.001 or less.

The "diagnostic accuracy" of a test, assay, or method concerns the ability of the test, assay, or method to distinguish between patients having diabetes or at risk for diabetes is based on whether the patients have a "clinically significant presence" of a fibrinogen αC domain peptide or hemoglobin polypeptide. By "clinically significant presence" is meant that the presence of the fibrinogen αC domain peptide or hemoglobin polypeptide in the patient (typically in a sample from the patient) is higher or lower than the predetermined cut-off point (or threshold value) for that fibrinogen αC domain peptide or hemoglobin polypeptide and therefore indicates that the patient has cancer for which the sufficiently high presence of that protein is a marker.

The terms "high degree of diagnostic accuracy" and "very high degree of diagnostic accuracy" refer to the test or assay for that fibrinogen αC domain peptide or hemoglobin polypeptide with the predetermined cut-off point correctly (accurately) indicating the presence or absence of the cancer. A perfect test would have perfect accuracy. Thus, for individuals who have diabetes, the test would indicate only positive test results and would not report any of those individuals as being "negative" (there would be no "false negatives"). In other words, the "sensitivity" of the test (the true positive rate) would be 100%. On the other hand, for individuals who did not have diabetes, the test would indicate only negative test results and would not report any of those individuals as being "positive" (there would be no "false positives"). In other words, the "specificity" (the true negative rate) would be 100%. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test.

Changing the cut point or threshold value of a test (or assay) usually changes the sensitivity and specificity but in a qualitatively inverse relationship. For example, if the cut point is lowered, more individuals in the population tested will typically have test results over the cut point or threshold value. Because individuals who have test results above the cut point are reported as having the disease, condition, or syndrome for which the test is being run, lowering the cut point will cause more individuals to be reported as having positive results (i.e., that they have cancer). Thus, a higher proportion of those who have cancer will be indicated by the test to have it. Accordingly, the sensitivity (true positive rate) of the test will be increased. However, at the same time, there will be more false positives because more people who do not have the disease, condition, or syndrome (i.e., people who are truly "negative") will be indicated by the test to have fibrinogen αC domain peptide or hemoglobin polypeptide values above the cut point and therefore to be reported as positive (i.e., to have the disease, condition, or syndrome) rather than being correctly indicated by the test to be negative. Accordingly, the specificity (true negative rate) of the test will be decreased. Similarly, raising the cut point will tend to decrease the sensitivity and increase the specificity. Therefore, in assessing the accuracy and usefulness of a proposed medical test, assay, or method for assessing a patient's condition, one should always take both sensitivity and specificity into account and be mindful of what the cut point is at which the sensitivity and specificity are being reported because sensitivity and specificity may vary significantly over the range of cut points.

There is, however, an indicator that allows representation of the sensitivity and specificity of a test, assay, or method over the entire range of cut points with just a single value. That indicator is derived from a Receiver Operating Characteristics ("ROC") curve for the test, assay, or method in question. See, e.g., Shultz, "Clinical Interpretation Of Laboratory Procedures," chapter 14 in Teitz, Fundamentals of Clinical Chemistry, Burtis and Ashwood (eds.), 4th edition 1996, W.B. Saunders Company, pages 192-199; and Zweig et al., "ROC Curve Analysis: An Example Showing The Relationships Among Serum Lipid And Apolipoprotein Concentrations In Identifying Patients With Coronory Artery Disease," Clin. Chem., 1992, 38(8): 1425-1428.

An ROC curve is an x-y plot of sensitivity on the y-axis, on a scale of zero to one (i.e., 100%), against a value equal to one minus specificity on the x-axis, on a scale of zero to one (i.e., 100%). In other words, it is a plot of the true positive rate against the false positive rate for that test, assay, or method. To construct the ROC curve for the test, assay, or method in question, patients are assessed using a perfectly accurate or "gold standard" method that is independent of the test, assay, or method in question to determine whether the patients are truly positive or negative for the disease, condition, or syndrome (for example, coronary angiography is a gold standard test for the presence of coronary atherosclerosis). The patients are also tested using the test, assay, or method in question, and for varying cut points, the patients are reported as being positive or negative according to the test, assay, or method. The sensitivity (true positive rate) and the value equal to one minus the specificity (which value equals the false positive rate) are determined for each cut point, and each pair of x-y values is plotted as a single point on the x-y diagram. The "curve" connecting those points is the ROC curve.

The area under the curve ("AUC") is the indicator that allows representation of the sensitivity and specificity of a test, assay, or method over the entire range of cut points with just a single value. The maximum AUC is one (a perfect test) and the minimum area is one half. The closer the AUC is to one, the better is the accuracy of the test.

By a "high degree of diagnostic accuracy" is meant a test or assay (such as the test of the invention for determining the clinically significant presence of fibrinogen αC a domain peptide or hemoglobin polypeptide, which thereby indicates the presence of diabetes) in which the AUC (area under the ROC curve for the test or assay) is at least 0.70, desirably at least 0.75, more desirably at least 0.80, preferably at least 0.85, more preferably at least 0.90, and most preferably at least 0.95.

By a "very high degree of diagnostic accuracy" is meant a test or assay in which the AUC (area under the ROC curve for the test or assay) is at least 0.875, desirably at least 0.90, more desirably at least 0.925, preferably at least 0.95, more preferably at least 0.975, and most preferably at least 0.98.

Optionally, expression of other peptide biomarkers for cancer are also determined as further indication of whether or not the subject is carrying a cancer. For example, peptides with mass to charge (m/z) ratio of about 7558, 7933, 1418 or 15168 are detected. Additionally, expression of other known biomarkers for a particular cancer are also determined as further indication of whether or not the subject is carrying a cancer. For example, alpha-fetoprotein (AFP), beta-2-microglobulin (B2M), Bladder tumor antigen (BTA), CA 15-3, CA 27.29, CA 125, CA 72-4, CA 19-9, Calcitonin, Carcinoembryonic antigen (CEA), Chromogranin A, Serum gamma globulin, Serum Her-2/neu, Human chorionic gonadotropin (HCG), Lipid Associated Sialic Acid in Plasma (LASA-P), NMP22, Neuron-specific enolase (NSE), Prostate-specific antigen (PSA), Prostatic acid phosphatase (PAP), Prostate-specific membrane antigen (PSMA), S-100, TA-90, Thyroglobulin, or Tissue polypeptide antigen (TPA) is detected.

The fibrinogen αC domain peptide, hemoglobin polypeptide and the additional biomarkers are detected in any suitable manner, but is typically detected by contacting a sample from the patient with an antibody which binds the fibrinogen αC domain peptide, hemoglobin polypeptide or biomarker and then detecting the presence or absence of a reaction product. The antibody may be monoclonal, polyclonal, chimeric, or a fragment of the foregoing, as discussed in detail above, and the step of detecting the reaction product may be carried out with any suitable immunoassay. The sample from the subject is typically a biological fluid as described above, and may be the same sample of biological fluid used to conduct the method described above.

Expression of a fibrinogen αC domain peptide or hemoglobin polypeptide also allows for the course of treatment of cancer to be monitored. In this method, a biological sample is provided from a subject undergoing treatment, e.g., surgical, chemotherapeutic or hormonal treatment, for a cancer. If desired, biological samples are obtained from the subject at various time points before, during, or after treatment. Expression of a fibrinogen αC domain peptide hemoglobin polypeptide is then determined and compared to a reference, e.g. control whose cancer state is known. The reference sample has been exposed to the treatment. Alternatively, the reference sample has not been exposed to the treatment. Optionally, such monitoring is carried out preliminary to a second look surgical surveillance procedures and subsequent surgical surveillance procedures. For example, samples may be collected from subjects who have received initial surgical treatment for cancer and subsequent treatment with antineoplastic agents for that cancer to monitor the progress of the treatment.

If the reference sample is from a subject that does not have cancer, a similarity or an increase in the amount of the fibrinogen αC domain peptide or hemoglobin polypeptide in the test sample and the reference sample indicates that the treatment is efficacious. However, a decrease in the amount of the fibrinogen αC domain peptide in the test sample and the reference sample indicates a less favorable clinical outcome or prognosis. Whereas an increase in the amount of the hemoglobin polypeptide in the test sample and the reference sample indicates a less favorable clinical outcome or prognosis.

By "efficacious" is meant that the treatment leads to an increase in the amount of a fibrinogen αC domain peptide, a decrease in the amount of a hemoglobin polypeptide or a decrease in size, prevalence, or metastatic potential of a tumor in a subject. Assessment of cancer is made using standard clinical protocols. Efficacy is determined in association with any known method for diagnosing or treating the particular tumor.

Expression of a fibrinogen αC domain peptide or a hemoglobin polypeptide also allows the identification of patients who will be responsive to systemic, e.g., chemotherapeutic, hormonal or radiation therapy. In this method, a biological sample is provided from a subject prior to undergoing surgical treatment, for a cancer. Expression of a fibrinogen αC domain peptide is then determined and compared to a biological sample obtained from the subject after surgical removal of the cancer. The patient will likely be responsive to systemic treatment if the amount of the fibrinogen αC domain polypeptide increases after surgical removal the cancer. In contrast a the patient will likely not be responsive to systemic treatment if the amount of the polypeptide remains constant or decreases after surgical removal of the cancer. The patient will likely be responsive to systemic treatment if the amount of the hemoglobin polypeptide decreases after surgical removal the cancer. In contrast, a the patient will likely not be responsive to systemic treatment if the amount of the hemoglobin polypeptide remains constant or increases after surgical removal of the cancer Expression of the fibrinogen αC domain peptide, hemoglobin polypeptide or other cancer biomarkers (e.g., Her-2 or CA-125) is determined at the protein or nucleic acid level using any method known in the art. For example, Northern hybridization analysis using probes which specifically recognize one or more of these sequences can be used to determine gene expression. Alternatively, expression is measured using reverse-transcription-based PCR assays, e.g., using primers specific for the differentially expressed sequence of genes. Expression is also determined at the protein level, i.e., by measuring the levels of peptides encoded by the gene products described herein, or activities thereof. Such methods are well known in the art and include, e.g., immunoassays based on antibodies to proteins encoded by the genes. Any biological material can be used for the detection/quantification of the protein or Ws activity. Alternatively, a suitable method can be selected to determine the activity of proteins encoded by the marker genes according to the activity of each protein analyzed.

The subject is preferably a mammal. The mammal is, e.g., a human, non-human primate, mouse, rat, dog, cat, horse, or cow. Subjects are typically human females or human males. The methods are applicable to testing for cancer such as breast cancer, colon cancer, liver cancer, pancreatic cancer, ovarian cancer, prostate cancer, or lung cancer.

The subject has been previously diagnosed as carrying a cancer, and possibly has already undergone treatment for the cancer. Alternatively, the subject has not been previously diagnosis as carrying a cancer. The present invention is useful with all patients at risk for a cancer. Although each type of cancer has their own set of risk factors, the risk of developing cancer increases as with aged, gender, race and personal and family medical history. Other risk factors are largely related to lifestyle choices, while certain infections, occupational exposures and some environmental factors can also be related to developing cancer. Breast cancer risk factors include personal and family history of breast cancer, early menarche (first period before age 12), obesity, late onset of menopause (after age 50), alcohol abuse, smoking, lack of exercise, and delayed or absent child bearing. The risks of developing breast cancer increase exponentially after the age of 30.

Optionally, the subject is tested for carrying other indicators of susceptibility of developing cancer. For example, the subject is positive for BRAC1 or BRAC2.

Diagnosis of cancer is typically made through the identification of a mass on an examination, though it may also be through other means such as a radiological diagnosis, ultrasound, or the detection of a humoral marker such as CA-125, HER-2 or PSA. Treatment is typically through cytoreductive surgery, followed by treatment with antineoplastic agents such as docetaxel vinorelbine gemcitabine, capecitabine or a combinations of cyclophosphamide, methotrexate, and fluorouracil; cyclophosphamide, doxorubicin, and fluorouracil; doxorubicin and cyclophosphamide; doxorubicin and cyclophosphamide with paclitaxel; doxorubicin followed by CMF; or Cyclophosphamide, epirubicin and fluorouracil. In addition, many patients will require radiation therapy. In patients with breast cancer, tamoxifin therapy may also be required.

Immunoassays carried out in accordance with the present invention may be homogeneous assays or heterogeneous assays. In a homogeneous assay the immunological reaction usually involves the specific antibody (e.g., fibrinogen αC domain peptide or hemoglobin polypeptide), a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are radioimmunoassays, immunofluorescence methods, or enzyme-linked immunoassays.

Those skilled in the art will be familiar with numerous specific immunoassay formats and variations thereof, which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogeneous Specific Binding Assay Employing a Coenzyme as Label."

Antibodies are conjugated to a solid support suitable for a diagnostic assay (e.g., beads, plates, slides or wells formed from materials such as latex or polystyrene) in accordance with known techniques, such as precipitation. An antibody or antibody fragment that binds to CA-125 or CEA may optionally be conjugated to the same support, as discussed above. Antibodies as described herein may likewise be conjugated to detectable groups such as radiolabels (e.g., 35 S, 125 I, 131 I), enzyme labels (e.g., horseradish peroxidase, alkaline phosphatase), and fluorescent labels (e.g., fluorescein) in accordance with known techniques.

Diagnostic kits for carrying out the methods described herein are produced in a number of ways. In one embodiment, the diagnostic kit comprises (a) an antibody (e.g., fibrinogen αC domain peptide) conjugated to a solid support and (b) a second antibody of the invention conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. Alternatively, a test kit contains (a) an antibody, and (b) a specific binding partner for the antibody conjugated to a detectable group. Ancillary agents as described above may likewise be included. The test kit may be packaged in any suitable manner, typically with all elements in a single container along with a sheet of printed instructions for carrying out the test.

Example 1

General Methods

Patient Cohort and Sample Handling

Sixty-one pre-therapy patients with HER2-positive breast cancer and 61 healthy women controls were used for the study. For the case-control study, plasma from the patients was randomly split into a training set of 40 patients and 40 controls and a test set of 21 patients and 21 controls. The cancer and control samples were collected in the same way to avoid possible systemic bias. For the longitudinal study, plasma from another cohort of 28 patients with operable cancer underwent a pre-treatment plasma collection and were compared to plasma from a blood draw at least two-weeks after the completion of all treatments (post-treatment blood draw). These women were treated on neo-adjuvant protocols in which trastuzumab (herceptin) combined with chemotherapy was given prior to surgery. All stage II and III women underwent surgery, either mastectomy or wide excision (lumpectomy), and a combination of procedures were done on ipsilateral lymph nodes. Known axillary disease was removed surgically. For those undergoing wide-excision, breast radiation given after surgery was part of the local treatment. The clinical characteristics of the patients are listed in Table 1; some of these patients were deemed to have stage IV disease during treatment.

Blood was collected at the Dana Farber-Harvard Cancer Center under IRB-approved protocols. The entire case-control study was repeated on stored plasma held at −80° C. All samples were collected in tubes containing citrate buffer and processed immediately under same conditions prior to freezing. All samples were analyzed without information as to patient identities.

Plasma Fractionation

Plasma samples were fractionated with an anion exchange resin (Biosepra, Marlboro, Mass.) using stepwise pH elution in a 96 well filter plate format (Nalge Nunc, Naperville, Ill.). First, 50 μl of plasma was denatured in 75 μl of buffer U9 (9M urea, 2% CHAPS, 50 mM Tris-HCl pH 9) in a 96 well plate at 4° C. for 20 minutes while shaking.

Filter plates were loaded with 180 μl of the pretreated resin (washed with 5 bed volumes of 50 mM Tris-HCl pH9, 50% suspension in the wash buffer). This was followed by equilibration with buffer U1 (1M urea, 0.22% CHAPS, 50 mM Tris-HCl pH9), and then 50 μL of the denatured plasma samples were transferred to the equilibrated filter plate. An additional 50 μl buffer U1 was added into each well. The filter plate was shaken for 30 minutes at 4° C. to allow the binding of plasma proteins to the resin. The filter plate was spun into a collection plate labeled as "Fraction 1". An additional 100 μl of wash buffer 1 (50 mM Tris-HCl with 0.1% n-Octyl β-D-glucopyranoside (OGP), pH10) was added into the filter plate, which was shaken for 10 minutes at room temperature and spun-filtered into the same Fraction 1 collection plate. "Fraction 23" was obtained by washing the resin in the same manner with wash buffer 2 (100 mM NaPhosphate with 0.1% OGP pH7) and then with wash buffer 3 (100 mM NaAcetate with 0.1% OGP pH5). "Fraction 45" was obtained by washing the resin, with wash buffer 4 (100 mM NaAcetate with 0.1% OGP pH4) and wash buffer 5 (50 mM NaCitrate with 0.1% OGP pH3). Remaining denatured plasma prior to fractionation (75 μl) was diluted in 225 μl of PBS and labeled as "Fraction SC". All the collection plates were stored at −70° C. until proceeding with protein chip surface capture protocol.

Protein Chip Surface Capture

IMAC40 chip-binding surfaces, charged with CuSO4 were used and loaded into a 192 well Bioprocessor (Ciphergen, Calif.). A Tecan Genesis robotic workstation was used for liquid handling and all experiments were carried out at room temperature. Binding of proteins to the chip surface was performed by adding 70 μl of binding buffer and 10 μl of the indicated plasma fraction and vortexing for 30 minutes. The chips were then washed 3 times with 100 μl PBS and rinsed twice with 100 μl water. The Bioprocessor was disassembled and the chips were air dried for 10 minutes. At the end of the process, 1 μl of an energy absorbing molecule (EAM) solution (Cyano-4-hydroxycinnamic acid, CHCA) in 50% acetonitrile and 0.5% trifluoroacetic acid, was applied to each spot using a 96 channel Tecan Genmate robot. The chips were air dried for another 10 minutes, and then scanned immediately using the procedure outlined below.

Spectrum Data Collection

The chips were scanned using a PBSII-C instrument (Ciphergen, Calif.) equipped with an autoloader. SELDI software version 3.1 was used to control the parameters of data collection. The parameter settings were: High mass collection limit was 20000 m/z (mass to charge ratio). Optimization range was from 1000 to 10000 m/z, focused at 5500 m/z. The laser intensity used was optimized for each fraction. An automatic protocol was implemented to collect the data from each set of chips. One hundred twenty laser shots were fired across each spot and the resulting data collected, averaged and stored as the spectrum for that spot. The molecular weight accuracy of the system was calibrated with a peptide mixture immediately before scanning of each fraction. The spectra were labeled as Fraction m/z, where "SC" representing plasma fraction, "F23" representing fraction 2 and 3 combined, etc.

Spectrum Data Processing

The baselines were subtracted and the spectra normalized by the total ion current function using default parameter settings of the Ciphergen software. Peaks were defined as those peptides with a signal-to-noise ratio (S/N) above five. Biomarker candidates, i.e., peaks with similar m/z value across spectra, were detected using the following criteria, 1) peak intensity of five-fold over noise, 2) peaks present in a minimum of 10% of all spectra, and 3) the m/z of peaks differed across spectra by ≦0.3% of the m/z. Quality control procedures to detect individual spectrum failure and failed fractions[31] were applied. Failed spectra and fractions were eliminated from further analysis.

Two independent experiments with the same collection of samples were performed, one that was used immediately and one that was kept frozen for six months at −80° C. Before averaging the two experiment data sets, highly reproducible markers were determined between the data sets. The peaks were aligned allowing for 0.1% to 0.3% mass error between the two data sets. A correlation coefficient was calculated for each of the aligned peaks and only peaks with correlation coefficient higher than 0.5 were selected for averaging and biomarker detection. The 61 cancer and 61 control samples were randomly partitioned into a training set containing 40 cancer and 40 controls, and a test set containing the other 21 cancer and 21 controls. Biomarker selection was applied on the training set, validated on the test set and finally further validated on the pre- and post-surgery longitudinal study.

Biomarker Selection

Four methods to select biomarkers that segregate cancer patients from controls were used: Recursive Support Vector Machine (R-SVM)[32], Random Forest[33], T-test and Receiver Operating Characteristic (ROC) curve. The first two methods analyze multi-dimensional data and directly select important biomarkers that contribute the most to the classification of samples. The later two methods evaluate the importance of each marker independently, and the importance of these markers is reflected by p-value and relative ranking. For T-test, after calculating a p-value for each of the biomarkers, False Discovery Rate (FDR) control[34] was used to adjust the raw p-values and selected important biomarkers by the adjusted p-values. Biomarkers were discovered in two identical sets of plasma, one that was used immediately and one that was kept frozen for six months at −80° C. Peaks from both sets of plasma were aligned, peak identity defined and only candidates reproduced in both sets were designated candidate biomarkers.

Example 2

Biomarker Selection (Case-Control Study)

Table 1 shows the clinical characteristics of patients in the case-control study. The distribution of disease burden (stage) and hormone receptor content in primary tumors was similar in cases assigned to the learning and test sets. All tumors were HER2-positive by usual clinical criteria, and all tumors were high-grade breast cancers. Sixty-one breast cancer patients and controls were randomly partitioned into a training set containing 40 patients and 40 controls, and a test data set containing 21 patients and 21 controls. A total of 57 peaks passed selection criteria. Using cross validation and variable feature selection, R-SVM selected a seven biomarker set that was the optimal predictor of cancer status (FIG. 1, Supplemental Data). We then compared the biomarkers discovered by R-SVM to those found by Random Forest algorithm, t-test, and receiver operation curve algorithms. The results are summarized in Table 2. The seven-biomarkers selected by R-SVM were at least in the top 24 markers selected by the other methods. The top R-SVM-determined marker (F45_2661.4) was also ranked first in each of the other biomarker selection methods. Therefore, several peptides were "discovered" using very different statistical methods, and one peptide was ranked first by all methods of discovery.

R-SVM and Random Forest are statistical algorithms that build prediction models using combinations of individual features, in this case peptide peaks from the SELDI-TOF spectrographs. The best models from both methods were generated using the training set from the case-control study and validated on the test set. Unbiased external cross-validation error on training set and the prediction error on the test set by both methods are shown in FIG. 1A. With R-SVM, a minimum cross validation (CV) error of 22.5% was found with seven biomarkers on the training set. Validating the R-SVM selected model on the test data resulted in a similar error of 19.1%. The CV errors estimated by R-SVM with original as well as permuted class labels were shown in figure S1. The median CV error for any given number of model peaks is around 0.5 when class labels were randomly permuted, showing the CV error estimated by the R-SVM algorithm is unbiased. Since the CV error with original class labels is significantly lower than that of the permuted labels, significant classification information exists in the data. Using the Random Forest method, the CV error on training data set was 28.75%, and the error with the test data was 19.0%.

Figure 1B:
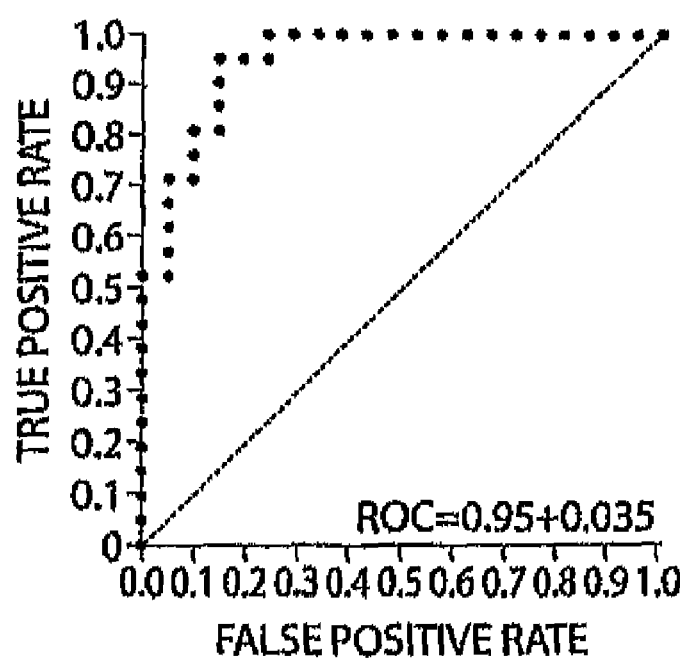
FIG. 1B is a schematic representation of a Receiver Operating Characteristics curve plotted using the 7 biomarker set obtained from the R-SVM analysis on the test data set. Area under the curve (AUC) is shown as mean±SD.

Receiver operating characteristics (ROC) curve is used to estimate the clinical performance of biomarkers, and results are summarized by the area under the ROC curve. An area under the curve (AUC)>0.9 is commonly used to identify markers useful in clinical practice[35]. Seven biomarkers obtained from R-SVM analysis were used to calculate the ROC on the test data set. FIG. 1B shows the ROC curve for the seven-biomarker set; the calculated AUC=0.95, indicating good discrimination segregating cancers vs. controls.

Figure 6A:
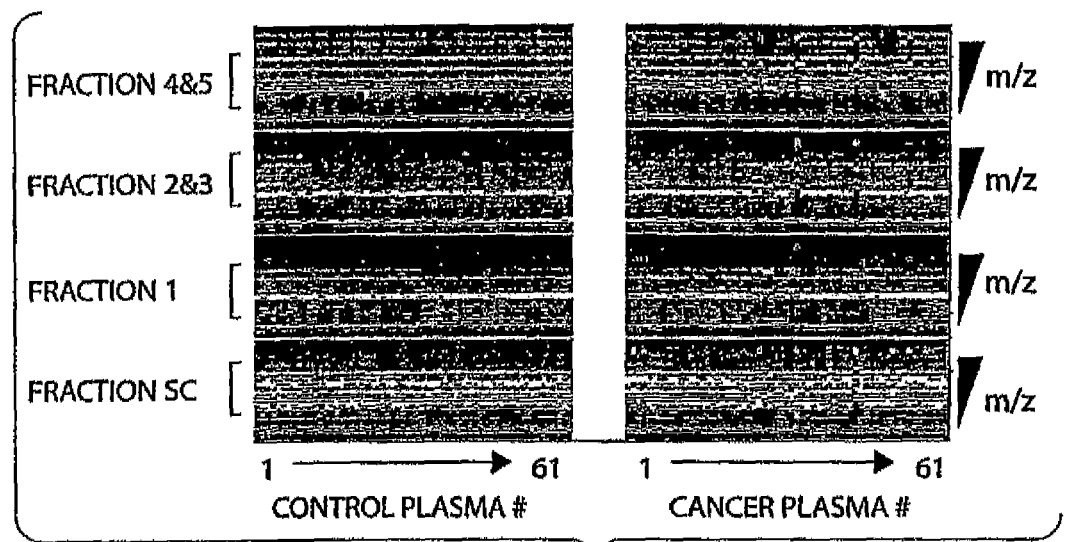
FIG. 6A are photographs of spectra showing the intensity of whole spectra in cancer and control plasma. The heights of each point in the spectra are converted into intensity and depicted in a heat map format where signal ranges from lower intensity shown in red to higher intensity in yellow.

Inconsistent sample collection, processing and storage may lead to inaccurate conclusions. These effects were estimated first by arbitrary designation of training and test sets from the 61 HER2-positive, untreated cases and controls (presented above); secondly by the use of peaks discovered independently in plasma used immediately and aliquots from the same blood draw stored for 6 months, and finally by visual inspection of intensity maps (heat maps) representing the entire spectrograph of cases and controls (FIG. 6A).

Figure 6B:
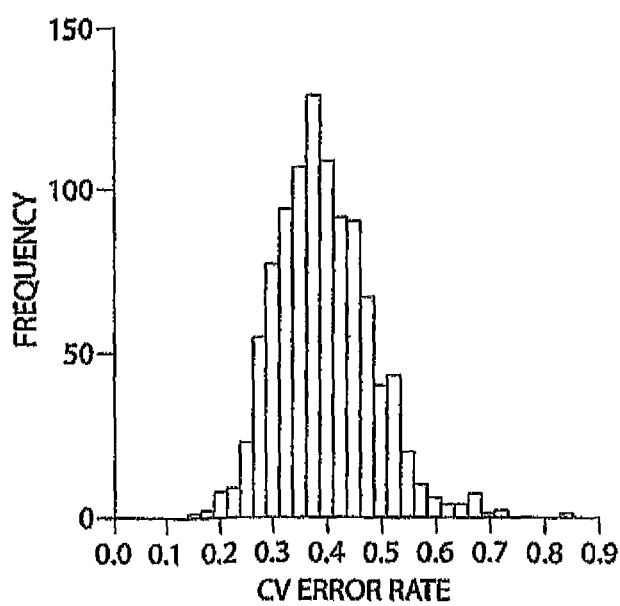
FIG. 6B is a histogram showing the distribution of cross validation errors (CV) of 1000 random sets of 8 biomarkers estimated by Support Vector Machine (SVM) analysis.

No individual spectra failed in either data set of the two independent experiments, separated by storage for 6 months. Fraction 1 failed in the second experiment and data was not used. After peak alignment, 98 peaks were identified in the samples analyzed immediately, 74 peaks were identified in the samples stored for six months and 57 peaks were reproduced in both plasma cohorts. Sample bias may lead to misinterpretation of case-control studies utilizing SELDI[36,37]. Using raw spectrographic data, we constructed composite heat maps from fractionated plasma in cases and controls, allowing detection of a systemic bias. No significant or pervasive differences were noted (FIG. 6A). Similarly, random sampling groups of seven biomarkers, and calculating the cross validation errors for prediction of cancer and controls, showed a random CV error that centered around 40%, consistent with the existence of informative markers in the case-control cohort (FIG. 6B). There does not appear to be strong sample or analytic bias in this study.

Example 3

Identification of a 2660 Dalton Marker

Figure 2A:
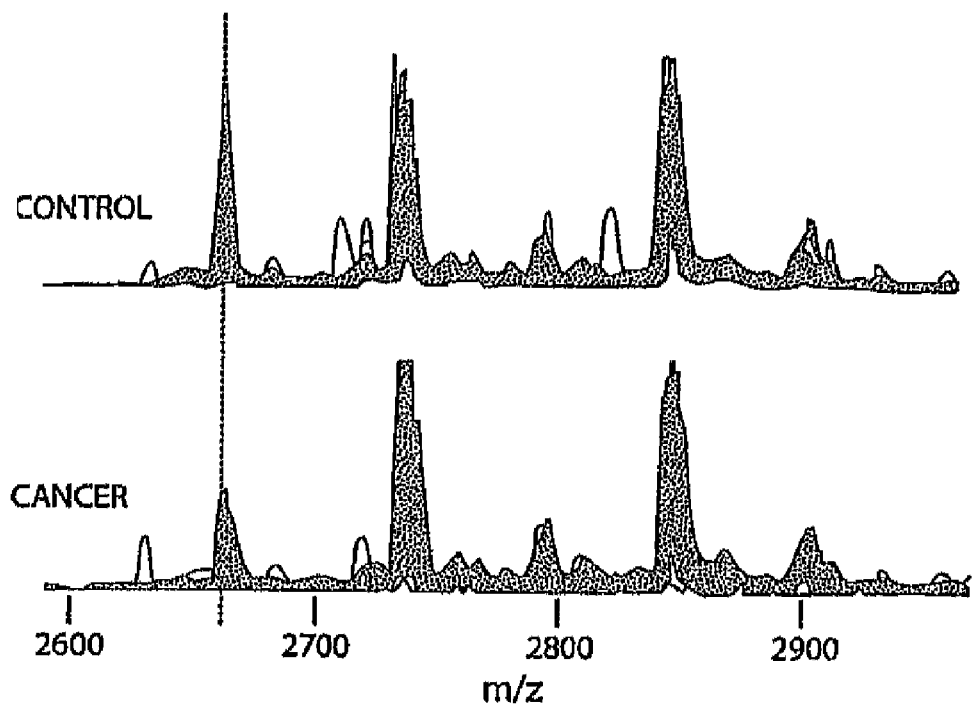
FIG. 2A is a schematic representation showing a representative spectra from cancer and control plasma. Spectra from all the samples of Fractions 2 and 3 in first run are overlaid, and grouped into control or cancer categories. The 2660 m/z peak is labeled with a dotted line.
Figure 2B:
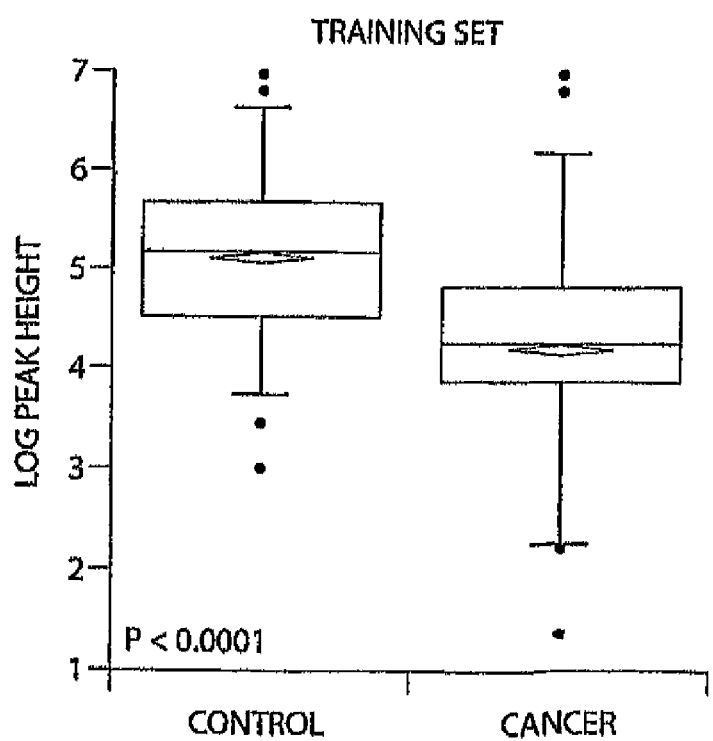
FIG. 2B is a box plot showing the peak height of the 2660 Dalton marker in the training data set. The Y-axis is the base 2 logarithm of the peak height. The data from fractions 4 and 5 was plotted using the box plot format where the whiskers extend to 95% of the data points, the horizontal line is the median and the diamond is the mean. The box includes data in the range from the $25^{th}$ to the $75^{th}$ quartile. The marker segregates cancer from control patients in the training set with a p-value less than 0.0001.
Figure 2C:
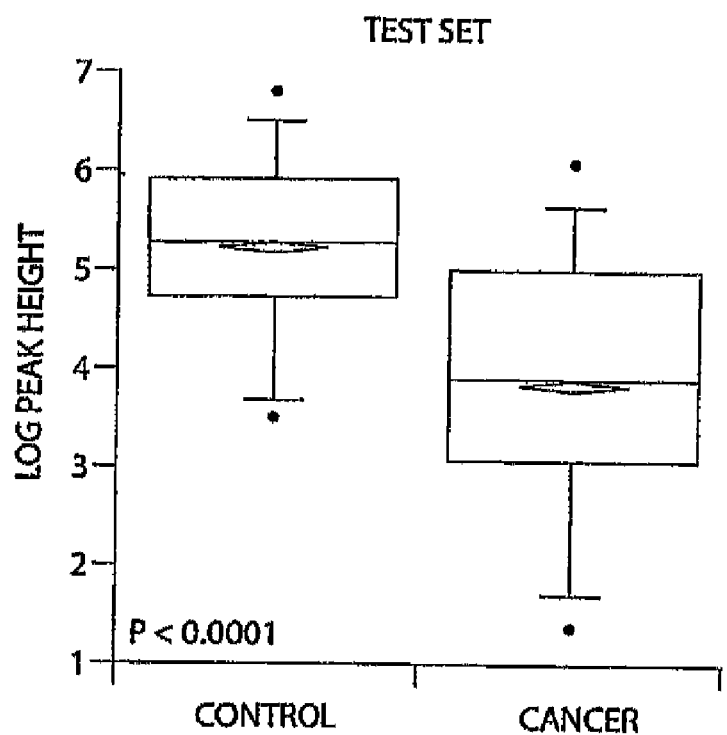
FIG. 2C is a box plot showing the peak height of the 2660 Dalton marker in test data set, drawn as in (B).
Figure 2D:
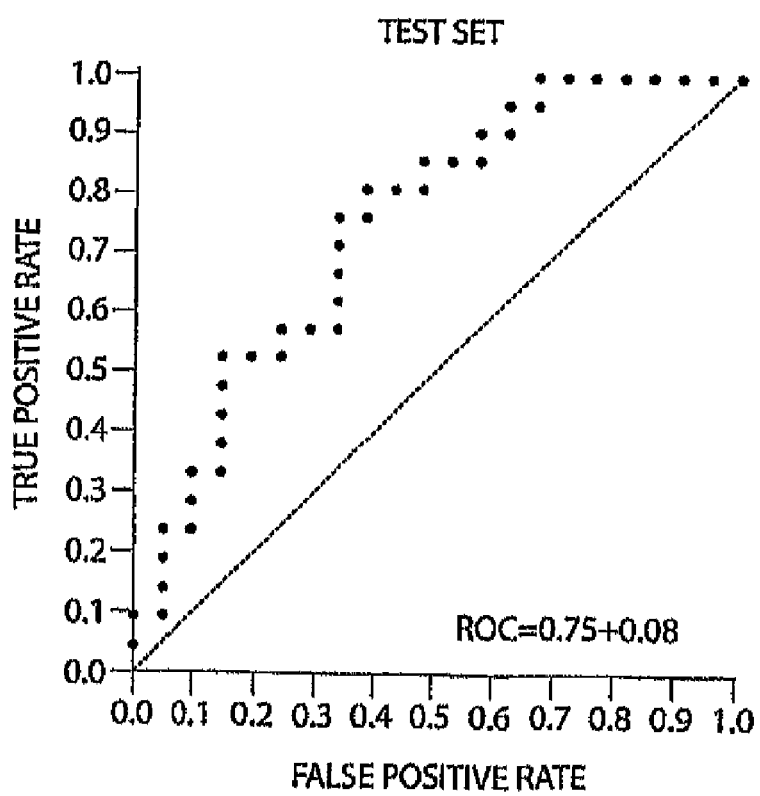
FIG. 2D is a ROC curve showing the 2660 Dalton marker used alone in the test data set. Area under the curve (AUC) value was shown as mean±SD.

A marker with an m/z value close to 2660 ranked as the most important according to all 4 statistical methods used; furthermore, this marker appeared in multiple fractions and in samples analyzed after prolonged freezing (Table 2). Superimposed spectra from all cancer and control samples in F23 in the 2600 to 2900 M.& range are shown in FIG. 2A. The overlaid peak height at 2660 is lower in plasma from cancer patients than in the plasma from unaffected controls. To quantitatively show this difference, FIGS. 2B and 2C show boxplots of the peak heights for this biomarker in cancer patients and unaffected controls in the training data set and the test data set, respectively. The expression of this peptide was significantly (T-test, p<0.0001) higher in control vs. cancer patients. The ROC was plotted using this single marker in the test data set and achieved an AUC=0.75, indicating discrimination using this single marker (FIG. 2D).

Using direct on-chip sequencing with a Q-TOF mass spectrometry instrument the peptide was identified with high probability (Mowse Score of 24) as a fragment from the c-terminus of Fibrinogen Alpha (FGA). This peptide encompasses amino acids 605-629 (referring to Swiss-Prot accession number P02671) of human Fibrinogen Alpha. The sequence of the peptide is DEAGSEADHEGTHSTKRGHAKSRPV ($FGA_{605-629}$). Furthermore, biomarkers with 2660 m/z value in other fractions (possibly leaking between fractions), were confirmed by sequencing to be the same peptide.

Example 4

Pre and Post-Surgery Validation (Longitudinal Study)

Figure 3:
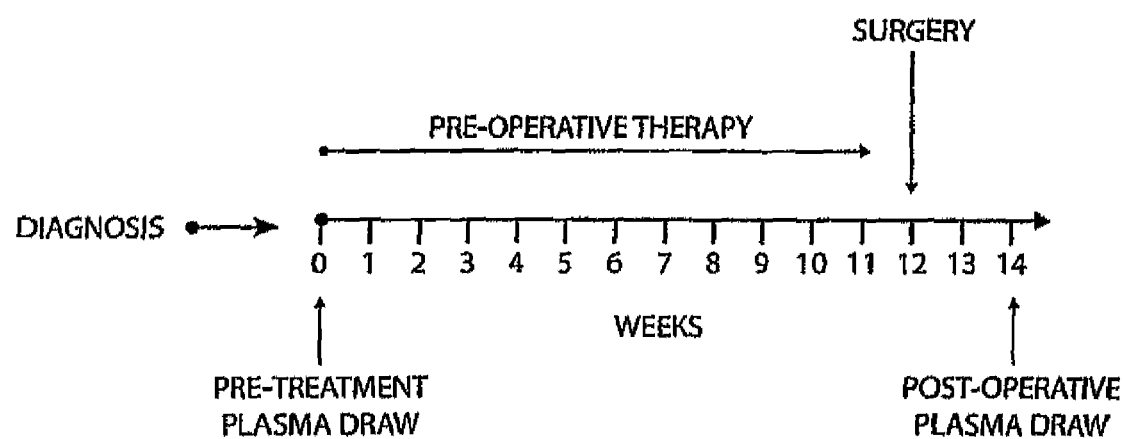
FIG. 3 is a schematic representation of the pre- and post-surgery study Pre-surgery samples were collected at diagnosis. Patients were treated on neo-adjuvant protocols in which trastuzumab (herceptin) combined with chemotherapy was given prior to surgery. Post-surgery plasma was obtained from a blood draw at least two-weeks after the surgery. A total of 28 pairs of pre- and post-surgery samples were collected

Local treatment of breast cancer alone renders most patients disease-free and eliminates clinically detectable disease. Therefore, there is an expectation that an important biomarker would revert to normal levels after neoadjuvant chemotherapy and surgical resection of the tumor. The change in the levels of biomarkers in pre and post-surgery samples were examined for validation of the case-control study. The post-surgery blood samples of a new cohort of twenty-eight patients were collected along with their corresponding pre-treatment blood samples. The schematics of pre and post-surgery sample collection are shown in FIG. 3. Patient clinical characteristics for this pre and post-surgery population are listed in Table 1 (pre-post surgery study).

Figure 4A:
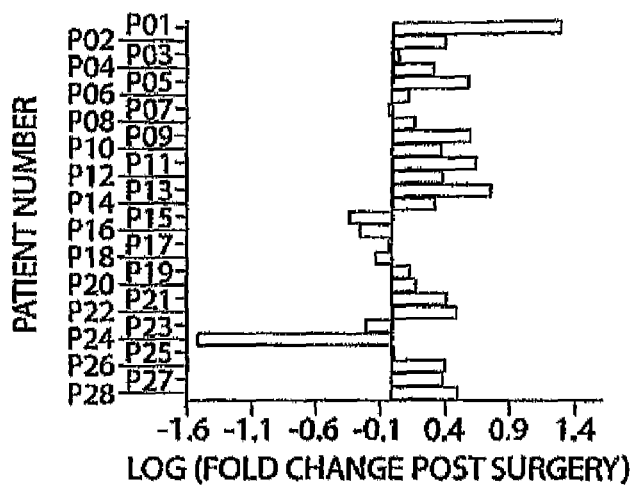
FIG. 4A is a bar chart showing the fold change post-surgery of $FGA_{605-629}$ in 28 patients. Individual patients are shown on the vertical axis and the logarithm of the fold-change is plotted on the horizontal axis; a declining level of the marker is shown to the left of center, and an increasing marker is shown to the right.
Figure 4B:
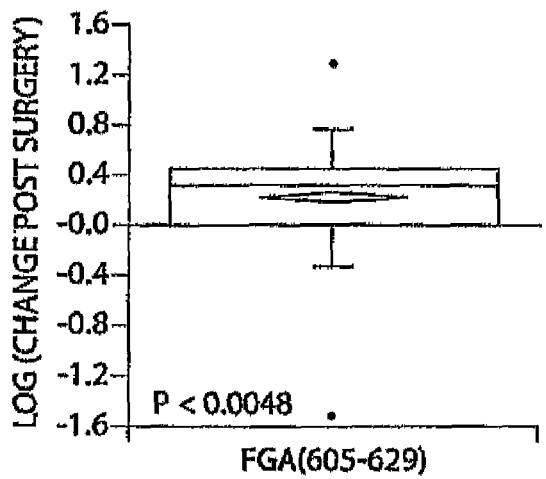
FIG. 4B is a box plot showing the log fold change in peak height of $FGA_{605-629}$ post-surgery. The data from fraction 4 and 5 was plotted using the box plot format where the whiskers extend to 95% of the data points, the horizontal line is the median and the diamond is the mean. The box includes data in the range from the $25^{th}$ to the $75^{th}$ quartile. $FGA_{605-629}$ returns towards normal levels post-surgery. The difference of the pre- and post-treatment level is significant (paired p=0.0048)
Figure 4C:
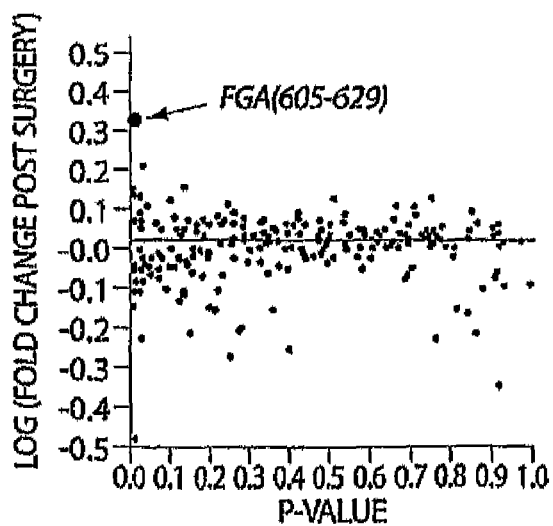
FIG. 4C is a scatter plot showing the log of median fold-change between pre- and post-treatment values versus the p value by paired t-test. The y-axis is the log of median fold change in peak height for biomarkers, and the x-axis is the p value of these biomarkers by paired t-test. The solid circle in the upper left hand corner represents the $FGA_{605-629}$ peak and has the greatest fold change and one of the lowest p-values post-surgery as compared to all the other peaks
Figure 5:
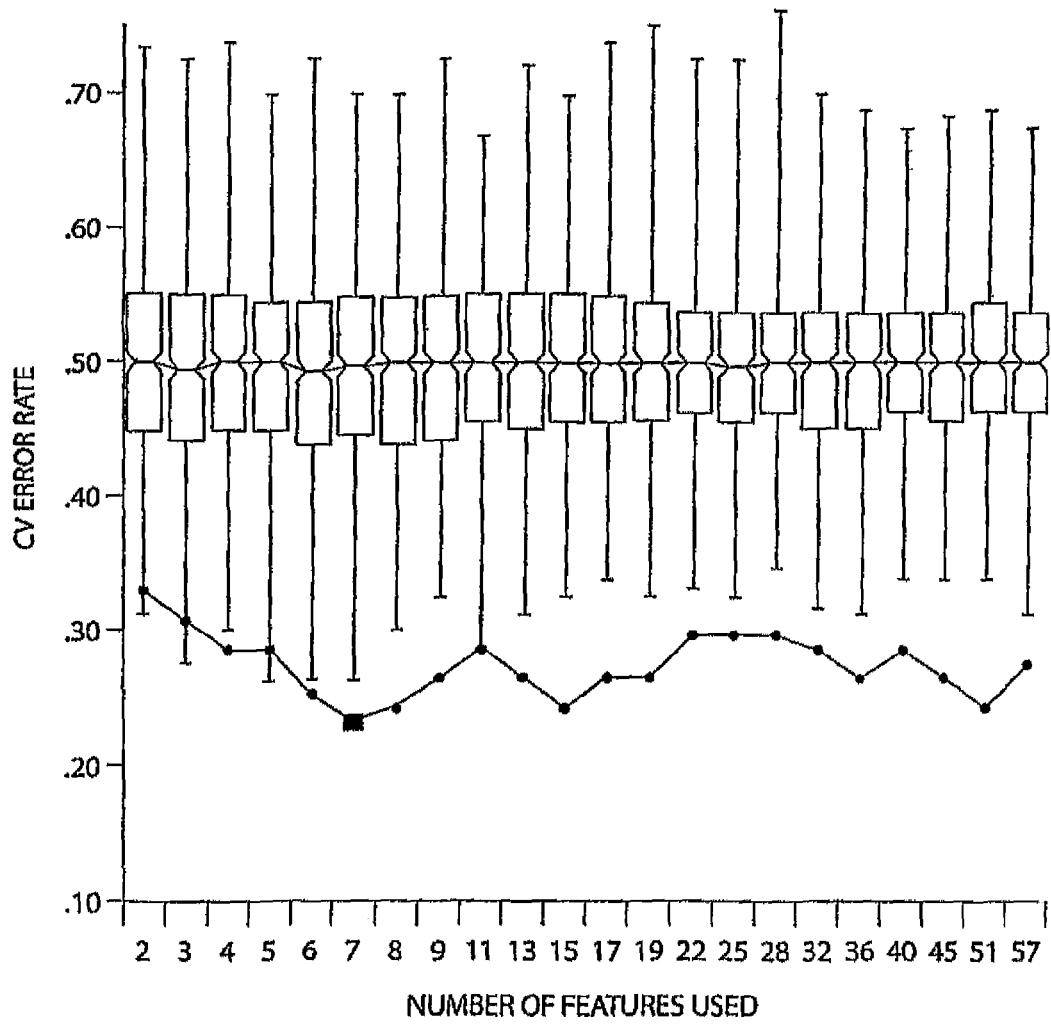
FIG. 5 is a box plot showing cross validation error distribution of correct and permuted class label data sets. The box plots represent the distribution of cross validation errors of data sets with class label permuted for each number of features ranging from 3 to 98. The marker selection and cross validation error calculation were repeated 500 times for each number of features. The line connecting the box plots is the mean of each of these cross validation errors. The data points connected by lines below each box plot are the cross validation errors of the original data set with the true class labels for that number of features.

The pre- and post-surgery samples were processed and analyzed together. A total of 229 peaks were detected using the same criteria described in the Materials and Methods. A pair-wise t-test was used to compare the pre- and post-surgery levels for each of the 229 peaks. The majority of the 28 patients had increased level of $FGA_{605-629}$ post-surgery as shown in FIG. 4A. Overall, $FGA_{605-629}$ was significantly higher in post-surgery patients compared to pre-surgery patients (p<0.0048; FIG. 4B). FIG. 4C is a scatter plot of p-values indicating the significance of change in marker concentration post-surgery versus the logarithm of the median fold change post-surgery of all 229 markers. Compared to all other markers, the level of $FGA_{605-629}$ has the highest fold change (an increase toward normal levels) associated with one of the most significant p-values. Therefore, the pre- and post-surgery study confirmed that levels of $FGA_{605-629}$ return to normal after pre-operative chemotherapy and surgical resection of the tumor, validating its importance as a biomarker for HER2-positive breast cancer and suggesting $FGA_{605-629}$ is useful in monitoring therapy.

TABLE 1

Characteristics of the breast cancers in the study cohorts.

| | Tumor Characteristics[†] | | | | | | | | |
|---|---|---|---|---|---|---|---|---|---|
| | Estrogen Receptor[‡] | | | Progesterone Receptor[‡] | | | Stage[†] | | |
| | | | | | | | II or III | IV | |
| Sample cohort | Pos. (%) | Neg. (%) | NR[§]. | Pos. (%) | Neg. (%) | NR. | (%) | (%) | NR |
| Case-Control Learning Set | 25 (62.5) | 15 (37.5) | 0 | 25 (66) | 13 (34) | 2 | 36 (90) | 4 (10) | 2 |
| Case-Control Test Set | 12 (60) | 8 (40) | 1 | 11 (58) | 8 (42) | 2 | 16 (76) | 5 (24) | 0 |
| Pre- & Post-Surgery | 17 (61) | 11 (39) | 0 | 14 (54) | 12 (46) | 2 | 28 (100) | 0 | 1 |

[†]All tumors were HER2-positive
[‡]Estrogen and progesterone receptor content was determined by immunohistochemistry on pre-operative core needle biopsies and reported in the clinical record.
[†]Stage was determined pre-operatively by clinical criteria and reported in the clinical record.
[§]NR: Not reported

TABLE 2

Relative rank of seven markers selected by R-SVM using other statistical methods

| | Relative rank by different statistical methods | | |
|---|---|---|---|
| Marker Selected by R-SVM (rank order) | Random Forest[‡] | T-test[‡,†] | ROC[‡] |
| (1) F45__2661.4[†] | 1 | 1 | 1 |
| (2) SC__2660.7 | 7 | 3 | 3 |
| (3) SC__2953.9 | 4 | 6 | 5 |
| (4) SC__7932.7 | 9 | 7 | 7 |
| (5) F23__4576.3 | 6 | 12 | 10 |
| (6) SC__8922.5 | 19 | 14 | 22 |
| (7) SC__3158.3 | 22 | 23 | 24 |

[†]Biomarker designations explained in Materials and Methods
[‡]Markers determined by Random Forest are ranked by their mean decrease in gini distance (see supplemental methods); markers determined by T-test are ranked according to T-statistics; markers determined by ROC are ranked by the area under the ROC curve for each marker comparing cancer vs. control.
[†]The first four makers found by T-test were statistically different in cancer vs. control samples after adjustment for false discovery (adjusted p < 0.05).

REFERENCES (1) National Center for Health Statistics. SEER cancer statistics review, 1973-1995., US National Cancer Institute, 1998.
(2) Carter, C. L.; Allen, C.; Henson, D. E. *Cancer* 1989, 63, 181-7.
(3) Valagussa, P.; Bonadonna, G.; Veronesi, U. *Cancer* 1978, 41, 1170-8.
(4) Sorlie, T.; Perou, C. M.; Tibshirani, R.; Aas, T.; Geisler, S.; Johnsen, H.; Hastie, T.; Eisen, M. B.; van de Rijn, M.; Jeffrey, S. S.; Thorsen, T.; Quist, H.; Matese, J. C.; Brown, P. O; Botstein, D.; Eystein Lonning, P.; Borresen-Dale, A. L. *Proc Natl Acad Sci USA* 2001, 98, 10869-74.
(5) Sortie, T.; Tibshirani, R.; Parker, J.; Hastie, T.; Marron, J. S.; Nobel, A.; Deng, S.; Johnsen, H.; Pesich, R.; Geisler, S.; Demeter, J.; Perou, C. M.; Lonning, P. E.; Brown, P. O.; Borresen-Dale, A. L.; Botstein, D. *Proc Natl Acad Sci USA* 2003, 100, 8418-23.
(6) Wang, Z. C.; Lin, M.; Wei, L. J.; Li, C.; Miron, A.; Lodeiro, G.; Harris, L.; Ramaswamy, S.; Tanenbaum, D. M.; Meyerson, M.; Iglehart, J. D.; Richardson, A. *Cancer Res* 2004, 64, 64-71.
(7) Yarden, Y.; Sliwkowski, M. X. *Nat Rev Mol Cell Biol* 2001, 2, 127-37.
(8) schnitt, S. J. *J Natl Cancer Inst Monogr* 2001, 22-6.
(9) Perou, C. M.; Sortie, T.; Eisen, M. B.; van de Rijn, M.; Jeffrey, S. S.; Rees, C. A.; W Pollack, J. R.; Ross, D. T.; Johnsen, H.; Akslen, L. A.; Fluge, O.; Pergamenschikov, A.; Williams, C.; Zhu, S. X.; Lonning, P. E.; Borresen-Dale, A. L.; Brown, P. O.; Botstein, D. *Nature* 2000, 406, 747-52.
(10) Miller, A. B.; Baines, C. J.; To, T.; Wall, C. *Cmaj* 1992, 147, 1459-76.
(11) Seregni, E.; Coli, A.; Mazzucca, N. *Eur J Nucl Med Mol Imaging* 2004, 31 *Suppl* 1, S15-22. Epub 2004 May 4.
(12) Heer, K.; Kumar, H.; Read, J. R.; Fox, J. N.; Monson, J. R.; Kerin, M. J. *Clin Cancer Res* 2001, 7, 3491-4.
(13) Karande, A. A.; Sridhar, L.; Gopinath, K. S.; Adiga, P. R. *Int J Cancer* 2001, 95, 277-81.
(14) Tang, N.; Tornatore, P.; Weinberger, S. R. *Mass Spectront Rev* 2004, 23, 34-44.
(15) Seibert, V.; Wiesner, A.; Buschmann, T.; Meuer, J. *Pathol Res Pract* 2004, 200, 83-94.
(16) Grizzle, W. E.; Semmes, O. J.; Basler, J.; Izbicka, E.; Feng, Z.; Kagan, J.; Adam, B. L.; Troyer, D.; Srivastava, S.; Thornquist, M.; Zhang, Z.; Thompson, I. M. *Urol Oncol* 2004, 22, 337-43.
(17) Liu, J.; Zheng, S.; Yu, J. K.; Zhang, J. M.; Chen, Z. *J Zhejiang Univ Sci* 2005, 6, 4-10.
(18) Yu, J. K.; Chen, Y. D.; Zheng, S. *World J Gastroenterol* 2004, 10, 3127-31.
(19) Chen, Y. D.; Zheng, S.; Yu, J. K.; Hu, X. *Clin Cancer Res* 2004, 10, 8380-5.
(20) Tolson, J.; Bogumil, R.; Brunst, E.; Beck, H.; Elsner, R.; Humeny, A.; Kratzin, H.; Deeg, M.; Kuczyk, M.; Mueller, G. A.; Mueller, C. A.; Flad, T. *Lab Invest* 2004, 84, 845-56.
(21) Wilson, L. L.; Tran, L.; Morton, D. L.; Hoon, D. S. *Ann N Y Acad Sci* 2004, 1022, 317-22.
(22) Xiao, X.; Zhao, X.; Liu, J.; Guo, F.; Liu, D.; He, D. *Sci China C Life Sci* 2004, 47, 219-23.
(23) Wadsworth, J. T.; Somers, K. D.; Cazares, L. H.; Malik, G.; Adam, B. L.; Stack, B. C., Jr.; Wright, G. L., Jr.; Semmes, O. J. *Clin Cancer Res* 2004, 10, 1625-32.
(24) Soltys, S. G.; Le, Q. T.; Shi, G.; Tibshirani, R.; Giaccia, A. J.; Koong, A. C. *Clin Cancer Res* 2004, 10, 4806-12.
(25) Zhang, Z.; Bast, R. C., Jr.; Yu, Y.; Li, J.; Sokoll, L. J.; Rai, A. J.; Rosenzweig, J. M.; Cameron, B.; Wang, Y. Y.; Meng, X. Y.; Berchuck, A.; Van Haaften-Day, C.; Hacker, N. F.; de

(26) Wang, Z.; Yip, C.; Ying, Y.; Wang, J.; Meng, X. Y.; Lomas, L.; Yip, T. T.; Fung, E. T. *Clin Chem* 2004, 50, 1939-42.
(27) Becker, S.; Cazares, L. H.; Watson, P.; Lynch, H.; Semmes, O. J.; Drake, R. R.; Laronga, C. *Ann Surg Oncol* 2004, 11, 907-14.
(28) Villanueva, J.; Shaffer, D. R.; Philip, J.; Chaparro, C. A.; Erdjument-Bromage, H.; Olshen, A. B.; Fleisher, M.; Lilja, H.; Brogi, E.; Boyd, J.; Sanchez-Carbayo, M.; Holland, E. C.; Cordon-Cardo, C.; Scher, H. I.; Tempst, P. *J Clin Invest* 2006, 116, 271-84.
(29) Liotta, L. A.; Petricoin, E. F.; Villanueva, J.; Philip, J.; Entenberg, D.; Chaparro, C. A.; Tanwar, M. K.; Holland, E. C.; Tempst, P.; Villanueva, J.; Shaffer, D. R.; Philip, J.; Chaparro, C. A.; Erdjument-Bromage, H.; Olshen, A. B.; Fleisher, M.; Lilja, H.; Brogi, E.; Boyd, J.; Sanchez-Carbayo, M.; Holland, E. C.; Cordon-Cardo, C.; Scher, H. I.; Tempst, P. *J Clin Invest* 2006, 116, 26-30.
(30) Villanueva, J.; Philip, J.; Entenberg, D.; Chaparro, C. A.; Tanwar, M. K.; Holland, E. C.; Tempst, P. *Anal Chem* 2004, 76, 1560-70.
(31) Mani, D. R.; Gillette, M. A. In *Next Generation of Data-Mining Applications*; M., K., J., Z., Eds.; Wiley-IEEE Press: 2005.
(32) Zhang, X. G., Lu, X., Xu, X. Q., Leung, H. E., Wong, W. H. and Liu, J. S. *BMC Bioinformatics*, 2006, in revision
(33) Breiman, L. *Machine Learning* 2001, 45, 5-32.
(34) Duda, R. O. a. H., P. E. *Pattern Classification and Scene Analysis*; John Wiley & Sons: New York, 1973.
(35) Metz, C. E. *Semin Nucl Med* 1978, 8, 283-98.
(36) Gillette, M. A.; Mani, D. R.; Carr, S. A. *J Proteome Res* 2005, 4, 1143-54.
(37) Villanueva, J.; Philip, J.; Chaparro, C. A.; Li, Y.; Toledo-Crow, R.; DeNoyer, L.; Fleisher, M.; Robbins, R. J.; Tempst, P. *J Proteome Res* 2005, 4, 1060-72.
(38) Qu, Y.; Adam, B. L.; Yasui, Y.; Ward, M. D.; Cazares, L. H.; Schellhammer, P. F.; Feng, Z.; Semmes, O. J.; Wright, G. L., Jr. *Clin Chem* 2002, 48, 1835-43.
(39) Vlahou, A.; Laronga, C.; Wilson, L.; Gregory, B.; Fournier, K.; McGaughey, D.; Perry, R. R.; Wright, G. L.; Jr.; Semmes, O. J. *Clin Breast Cancer* 2003, 4, 203-9.
(40) Paweletz, C. P.; Trock, B.; Pennanen, M.; Tsangaris, T.; Magnant, C.; Liotta, L. A.; Petricoin, E. F., 3rd *Dis Markers* 2001, 17, 301-7.
(41) Ambroise, C.; McLachlan, G. J. *Proc Natl Acad Sci USA* 2002, 99, 6562-6.
(42) Baggerly, K. A.; Morris, J. S.; Wang, J.; Gold, D.; Xiao, L. C.; Coombes, K. R. *Proteomics* 2003, 3, 1667-72.
(43) Yasui, Y.; Pepe, M.; Thompson, M. L.; Adam, B. L.; Wright, G. L., Jr.; Qu, Y.; Potter, J. D.; Winget, M.; Thornquist, M.; Feng, Z. *Biostatistics* 2003, 4, 449-63.
(44) Ball, G.; Mian, S.; Holding, F.; Allibone, R. O.; Lowe, J.; Ali, S.; Li, G.; McCardle, S.; Ellis, I. O.; Creaser, C.; Rees, R. C. *Bioinformatics* 2002, 18, 395-404.
(45) Petricoin, E. F.; Ardekani, A. M.; Hitt, B. A.; Levine, P. J.; Fusaro, V. A.; Steinberg, S. M.; Mills, G. B.; Simone, C.; Fishman, D. A.; Kohn, E. C.; Liotta, L. A. *Lancet* 2002, 359, 572-7.
(46) Coombes, K. R.; Fritsche, H. A., Jr.; Clarke, C.; Chen, J. N.; Baggerly, K. A.; Morris, J. S.; Xiao, L. C.; Hung, M. C.; Kuerer, H. M. *Clin Chem* 2003, 49, 1615-23.
(47) Simpson-Haidaris, P. I.; Rybarczyk, B. *Ann N Y Acad Sci* 2001, 936, 406-25.
(48) Gray, A. J.; Park, P. W.; Broekelmann., T. J.; Laurent, G. J.; Reeves, J. T.; Stenmark, K. R.; Mecham, R. P. *J Biol Chem* 1995, 270, 26602-6.
(49) Thompson, W. D.; Smith, E. B.; Stirk, C. M.; Wang, J. *Blood Coagul Fibrinolysis* 1993, 4, 113-5.
(50) Francis, C. W.; Bunce, L. A.; Sporn, L. A. *Blood Cells* 1993, 19, 291-306; discussion 306-7.
(51) Greiling, D.; Clark, R. A. *J Cell Sci* 1997, 110 (Pt 7), 861-70.
(52) Skogen, W. F.; Senior, R. M.; Griffin, G. L.; Wilner, G. D. *Blood* 1988, 71, 1475-9.
(53) Ye, B.; Cramer, D. W.; Skates, S. J.; Gygi, S. P.; Pratomo, V.; Fu, L.; Horick, N. K.; Licklider, L. J.; Schorge, J. O.; Berkowitz, R. S.; Mok, S. C. *Clin Cancer Res* 2003, 9, 2904-11.
(54) O'Reilly, M. S.; Boehm, T.; Shing, Y.; Fukai, N.; Vasios, G.; Lane, W. S.; Flynn, E.; Birkhead, J. R.; Olsen, B. R.; Folkman, J. *Cell* 1997, 88, 277-85.
(55) Blackwell, K.; Haroon, Z.; Broadwater, G.; Berry, D.; Harris, L.; Iglehart, J. D.; Dewhirst, M.; Greenberg, C. *J Clin Oncol* 2000, 18, 600-8.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for facilitating the diagnosis of a breast cancer in a subject, comprising detecting a fibrinogen αC domain polypeptide consisting of SEQ ID No. 1, from a blood sample from said subject, wherein a decrease of said polypeptide in said sample compared to a normal control sample indicates the presence of breast cancer in said subject.

2. The method of claim 1, wherein said subject has previously been treated surgically or hormonally for said cancer.

3. The method of claim 1, further comprising detecting Alpha-fetoprotein (AFP), Beta-2-microglobulin (B2M), Bladder tumor antigen (BTA), CA 15-3, CA 27.29, CA 125, CA 72-4, CA 19-9, Calcitonin, Carcinoembryonic antigen (CEA), Chromogranin A, Serum gamma globulin, Serum Her-2/neu, Human chorionic gonadotropin (HCG), Lipid Associated Sialic Acid in Plasma (LASA-P), NMP22, Neuron-specific enolase (NSE), Prostate-specific antigen (PSA), Prostatic acid phosphatase (PAP), Prostate-specific membrane antigen (PSMA), S-IOO, TA-90, Thyroglobulin, or Tissue polypeptide antigen (TPA).

4. The method of claim 1, wherein said subject is BRAC1 or BRAC2 positive.

5. The method of claim 1, wherein said cancer is breast cancer, colon cancer, liver cancer, pancreatic cancer, ovarian cancer, prostate cancer, or lung cancer.

6. The method of claim 1, further comprising detecting a peptide with mass to charge (m/z) ratio of about 7558, 7933, 1418 or 15168.

7. The method of claim 1, wherein said fibrinogen αC domain polypeptide is detected electrophoretically, or immunochemically.

8. The method of claim 7, wherein said immunochemical detection is by radio-immune assay, immunofluorescence assay or by an enzyme-linked immunosorbant assay.

9. A method according to claim 1, wherein said subject has not been previously diagnosed as having cancer.

10. A method according to claim 1, wherein said subject has been previously diagnosed as having cancer.

11. A method of diagnosing a breast cancer in a subject comprising, detecting the presence of a fibrinogen αC domain polypeptide consisting of SEQ. ID No: 1 from a blood sample from the subject; determining the level of said fibrinogen αC domain polypeptide in said sample to provide a test value; and comparing the test value to a standard value, wherein a test value below the standard value is indicative of breast cancer.

12. The method of claim 11, wherein said test value is 2 fold lower than said standard value.

13. The method of claim 11, wherein said test value is 5 fold lower than said standard value.

14. The method of claim 11, wherein said test value is 10 fold lower than said standard value.

15. The method of claim 1, wherein said polypeptide is detected electrophoretically, or immunochemically.

* * * * *